(12) United States Patent
Parker et al.

(10) Patent No.: US 6,261,570 B1
(45) Date of Patent: Jul. 17, 2001

(54) LIVE ATTENUATED VIRUS VACCINES FOR WESTERN EQUINE ENCEPHALITIS VIRUS, EASTERN EQUINE ENCEPHALITIS VIRUS, AND VENEZUELAN EQUINE ENCEPHALITIS VIRUS IE AND IIIA VARIANTS

(75) Inventors: Michael D. Parker, Frederick; Jonathan F. Smith, Sabillasville; Bruce J. Crise, Frederick, all of MD (US); Mark Steven Oberste, Lilburn, GA (US); Shannon M. Schmura, Hagerstown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 08/991,840

(22) Filed: Dec. 16, 1997

Related U.S. Application Data

(60) Provisional application No. 60/053,652, filed on Jul. 24, 1997, and provisional application No. 60/047,162, filed on May 20, 1997.

(51) Int. Cl.[7] .............................. A61K 39/12; C12N 7/04; C12N 15/40
(52) U.S. Cl. .................................... 424/205.1; 424/218.1; 424/93.2; 435/235.1; 435/236; 435/320.1; 536/23.72
(58) Field of Search .................. 536/23.72; 435/235.1, 435/236, 320.1; 424/205.1, 218.1, 93.2

(56) References Cited

U.S. PATENT DOCUMENTS 5,185,440   2/1993  Davis .
5,505,947   4/1996  Johnston .

OTHER PUBLICATIONS

Davis et al Virology 212(1):102–110, 1995.*
Kuhn et al Virology 182:430–441, 1991.*
Wang et al Journal of Virology 68(6):3550–3557, 1994.*
Meyers et al Journal of Virology 70(3):1588–1595, Mar. 1996.*
Fraizer, G. et al. (1985) Isolation and preliminary characterization of mutants of Western equine encephalomyelitis virus with altered virulence in chicken. Biological Abstracts. vol. 80, No. 5, p. AB–506, Abstract No. 41179.
Hahn, C. S. et al. (1988) Western equine encephalitis virus is a recombinant virus. Proc. Natl. Acad. Sci. USA 85:5997–6001.
Weaver, S. C. et al. (1993) A comparison of the nucleotide sequences of Eastern and Western equine encephalomyelitis viruses with those of other alphaviruses and related RNA viruses. Virology 197:375–390.
Straus, J. H. and E. G. Strauss (1994) The Alphavirus: gene expression, replication, and evolution. Microbiol. Rev. 58:491–562.

* cited by examiner

*Primary Examiner*—Mary E. Mosher
(74) *Attorney, Agent, or Firm*—Elizabeth Arwine; Charles H. Harris

(57) ABSTRACT cDNAs coding for an infectious Western Equine Encephalitis virus (WEE) and infectious Venezuelan Equine Encephalitis virus variant IE (VEE IE) are disclosed in addition to cDNA coding for the structural proteins of Venezuelan Equine Encephalitis virus variant IIIA (VEE IIIA). Novel attenuating mutations of WEE and VEE IE and their uses are described. Also disclosed are attenuated chimearic alphaviruses and their uses.

22 Claims, 7 Drawing Sheets

LIVE ATTENUATED VIRUS VACCINES FOR WESTERN EQUINE ENCEPHALITIS VIRUS, EASTERN EQUINE ENCEPHALITIS VIRUS, AND VENEZUELAN EQUINE ENCEPHALITIS VIRUS IE AND IIIA VARIANTS

This application claims the benefit of U.S. Provisional Application No. 60/047,162 filed on May 20, 1997, and U.S. Provisional Application no. 60/053,652 filed on Jul. 24, 1997.

Western equine encephalitis (WEE), eastern equine encephalitis (EEE) and Venezuelan equine encephalitis virus (VEE) are members of the alphavirus genus of the family Togaviridae which is comprised of a large group of mosquito-borne RNA viruses found throughout much of the world. The viruses normally circulate among rodent or avian hosts through the feeding activities of a variety of mosquitoes. Epizootics occur largely as a result of increased-mosquito activity after periods of increased rainfall. Western equine encephalitis virus (WEE) was first recognized in 1930 and causes periodic outbreaks of disease in equines. The virus has been detected over much of the western hemisphere from Argentina north to the more temperate regions of central Canada (For a review, see Reisen and Monath [1988] in *The Arboviruses: Epidemiology and Ecology, Vol. V*. CRC Press, Inc. Boca Raton). Similarly, EEE was first isolated in Virginia and New Jersey in 1933 (Ten Broeck, C. et al. [1935] *J. Exp. Med.* 62:677) and is now known to be focally endemic throughout much of the northern portion of South America, Central America and the eastern part of Mexico and the United States. Venezuelan equine encephalitis virus has six serological subtypes (I–VI). Two of these subtypes, I and III have multiple variants, two of these variants are of particular interest in this application, variant IE,and variant IIIA also called Mucambo virus. A live, attenuated vaccine (TC-83) for VEE IA/B has been used for immunization equines and at-risk laboratory and field personnel (Birge et al. [1961] *Am. J. Hyg.* 73:209–218; Pittman et al. [1996] *Vaccine* 14:337–343). The vaccine was credited with helping to limit the northward spread of a serious epizootic of VEE originating in South America in the late 1960's. However, the VEE I/AB vaccines have not yet been licensed by the Food and Drug Administration and have been shown to be effective in preventing disease from VEE IA/B infection only. The current VEE vaccines do not adequately protect against the VEE IE variant or the VEE IIIA variant, as disease has occurred in laboratory workers successfully vaccinated with a vaccine derived from VEE IA/B. In addition, recent unprecedented outbreaks of VEE IE in populations of horses in Mexico indicate a need for a VEE IE vaccine. The lack of adequate cross protection with existing IA/B vaccines documents the need for a VEE IE-specific and a VEE IIIA-specific vaccine.

The vaccines currently in veterinary use for WEE, EEE and VEE IA/B throughout the United States and Canada are formalin-inactivated preparations. Inactivated vaccines for EEE and WEE are also available for use by at-risk laboratory personnel. These inactivated vaccines are poorly immunogenic, require multiple inoculations with frequent boosters and generally result in immunity of short duration. The shortcomings of the available vaccines indicate a need for the development of new vaccines of high immunogenicity which induce a longer lasting immunity for protection against WEE, EEE and VEE subtypes IE and IIIA.

SUMMARY OF THE INVENTION

The present invention satisfies the need mentioned above.

In this application are described live attenuated vaccines for WEE, EEE, VEE IE and VEE IIIA which may provide higher level immunity in humans and equines for many years, and possibly for life. In addition, very large numbers of vaccine doses can be produced from significantly less starting materials than is possible with the existing inactivated products. The vaccine preparations of the present invention comprise full-length cDNA copies of the genomes of WEE or VEE IE which have been altered such that the RNA produced from the cDNA, and the virus produced therefrom is attenuated and useful as a live vaccine for human and veterinary use. The vaccine preparations for VEE IIIA and EEE are novel chimeric viruses which include the newly discovered structural protein genes of VEE IIIA.

The classic methods of deriving live-attenuated vaccines (blind passage in cell cultures) generally result in heterogeneous and undefined products, hence recent attempts to make live vaccines for alphaviruses have relied on genetic engineering procedures.

The alphavirus genome is a single-stranded, positive-stranded RNA approximately 11,400 nucleotides in length. The 5' two-thirds of the genome consist of a non-coding region of approximately 48 nucleotides followed by a single open reading frame of approximately 7,500 nucleotides which encodes the viral replicase/transcriptase. The 3' one-third of the genome encodes the viral structural proteins in the order C-E3-E2-6 K-E1, each of which are derived by proteolytic cleavage of the product of a single open reading frame of approximately 3700 nucleotides. The sequences encoding the structural proteins are transcribed as a 26S mRNA from an internal promoter on the negative sense complement of the viral genome. The nucleocapsid (C) protein possesses autoproteolytic activity which cleaves the C protein from the precursor protein soon after the ribosome transits the junction between the C and E3 protein coding sequence. Subsequently, the envelope glycoproteins E2 and E1 are derived by proteolytic cleavage in association with intracellular membranes and form heterodimers. E2 initially appears in the infected cell as a precursor, pE2, which consists of E3 and E2. After extensive glycosylation and transit through the endoplasmic reticulum and the golgi apparatus, E3 is cleaved from E2 by furin-like protease activity at a cleavage site having a consensus sequence of RX(K/R)R, with X being one of many amino acids present in the different viruses, and with the cleavage occuring after the last arginine residue. Subsequently, the E2/E1 complex is transported to the cell surface where it is incorporated into virus budding from the plasma membrane (Strauss and Strauss [1994] *Microbiological Rev.* 58: 491–562). All documents cited herein supra and infra are hereby incorporated in their entirety by reference thereto.

Because the genome of alphavirus is a positive-stranded RNA, and infectious upon transfection of cells in culture, an "infectious clone" approach to vaccine development is particularly suitable for the alphaviruses. In this approach, a full-length cDNA clone of the viral genome is constructed downstream from a RNA polymerase promoter, such that RNA which is equivalent to the viral genome can be transcribed from the DNA clone in vitro. This allows site-directed mutagenesis procedures to be used to insert specific mutations into the DNA clone, which are then reflected in the virus which is recovered by transfection of the RNA.

Previous work with infectious clones of other alphaviruses has demonstrated that disruption of the furin cleavage site results in a virus which incorporates pE2 into the mature virus. Davis et al. (1995, supra) found that disruption of the furin cleavage site in an infectious clone of VEE is a lethal mutation. Transfection of BHK cells with RNA transcribed from this mutant clone resulted in the release of non-infectious particles. However, a low level of infectious virus was produced which contained secondary suppressor mutations such that virus containing pE2 was fully replication competent and subsequently shown to be avirulent but capable of elliciting immunity to lethal virus challenge in a variety of animal species.

The genetic basis for attenuation of the VEE TC-83 vaccine and certain laboratory strains of VEE virus have been studied extensively and has led to the development of improved live, attenuated vaccine candidates (Kinney et al. 1993, supra, Davis et al. 1995, supra). The approach used in this application is similar to that used for VEE, however, following the VEE example exactly did not result in an adequate vaccine for WEE. Changes in the procedure used for VEE were required, none of which could have been predicted from the VEE work, in order to produce the attenuated live WEE virus of the present invention.

Based upon a comparison of the structural protein gene sequences of WEE and other alphaviruses, the probable furin cleavage site of WEE strain CBA/87 virus is RRPKR. The presence of the extra arginine when compared to the conscensus (RX(R/K)R) alphavirus cleavage site indicated that the cleavage at this site might be more complex than that observed with VEE virus. It was necessary therefore to prepare two deletion mutations in the E3-E2 cleavage site of the full-length clone, one which lacks five amino acids and one which lacks four amino acids since it was unknown which mutation, if any, would produce an attenuated virus. The residual arginine in the full-length clone lacking only four amino acids was of concern due to the possibility that other mutations might arise due to the presence of the extra arginine resulting in cleavage by cellular proteases at that site and producing an apparently wild type virus with respect to cleavage of pE2.

Transfection of cultured cells with RNA transcribed from an infectious clone of WEE lacking the furin cleavage site yielded viruses which contained the pE2 of WEE in the mature virus but which were not replication competent. During intracellular replication of the RNA, mutations arise at low frequency, resulting in a small number of replication competent virus. Sequence analysis of these viruses has shown that the lethal effect of the deletion mutations was alleviated by the appearance of second site mutations in the E2 glycoprotein. These viruses are attenuated in mice when administered by subcutaneous or intracranial inoculation. The mice produce high titer neutralizing and ELISA antibody and are protected against a lethal challenge of parental virulent WEE virus.

Therefore, in one aspect of the invention, the invention pertains to the isolation of a cDNA sequence coding for an infectious western equine encephalitis (WEE) virus RNA transcript. DNA representing the entire genome, not previously available, was prepared by polymerase chain reaction using a series of primer pairs based upon the partial genome sequences previously deposited in Genbank. The 5' and 3' ends of the viral genome were unknown and difficult to obtain. The terminal sequence was necessary for efficient replication of the virus since substitution of ends from a similar virus with similar but not identical sequences resulted in an extremely attenuated virus. In order to determine the correct sequence at the 5' end, a protocol called rapid amplification of cDNA ends (5'-RACE) was used. The full length infectious clone is useful in the production of virulent WEE virus, and introducing and testing attenuating mutations. The production of virulent virus is essential for a formal measure of the degree of attenuation achieved with candidate attenuating mutations and a formal determination of the rate at which reversion to virulence might occur.

In another aspect of the invention, the invention pertains to the isolation of a cDNA sequence coding for an infectious Venezuelan equine encephalitis virus IE variant (VEE IE) virus RNA transcript (SEQ ID NO: 2). Using oligonucleotides specific to genomic RNA of a VEE IE isolate (GenBank accession no. U34999) (Oberste, et al. [1996] *Virology* 219:314–320), reverse transcriptase polymerase chain reaction was carried out to generate numerous cDNA fragments which were subsequently cloned and used to assemble full-length CDNA of VEE IE. The full length infectious clone is useful, for example, in the production of virulent VEE IE virus, and introducing and testing attenuating mutations.

In the case of VEE IIIA, the structural protein genes were removed from a full length clone of VEE IA/B and replaced by the VEE IIIA structural genes. The IIIA structural gene sequences were prepared by RT-PCR and include the IIIA 26S promoter and the 3' nontranslated region (3' NTR) flanking the sequences for the structural proteins (SEQ ID NO:3). The VEE IIIA 3' NTR was then replaced with the VEE IA/B NTR, and the modified sequence was cloned back into the VEE IA/B full length clone. The result was a clone in which the nonstructural protein gene sequences were from VEE IA/B and the structural protein gene sequences from VEE IIIA. The virus produced from this chimeric clone replicated efficiently in cell culture, and proved to be completely attenuated in mice. In addition, it was highly immunogenic and protected the vaccinated mice against challenge with virulent, wild-type Mucambo virus (VEE IIIA).

Portions of the cDNA sequences described above are useful as probes to diagnose the presence of virus in samples, and to define naturally occuring variants of the virus. These cDNAs also make available polypeptide sequences of WEE antigens, EEE antigens, VEE IE antigens, and VEE IIIA structural polypeptide antigens encoded within the respective genomes and permits the production of polypeptides which are useful as standards or reagents in diagnostic tests and/or as components of vaccines. Antibodies, both polyclonal and monoclonal, directed against WEE epitopes, EEE epitopes, VEE IE epitopes, or VEE IIIA epitopes contained within these polypeptide sequences are also useful for diagnostic tests, as therapeutic agents, and for screening of antiviral agents.

Accordingly, with respect to polynucleotides, some aspects of the invention are: a purified WEE polynucleotide; a recombinant WEE polynucleotide; a recombinant polynucleotide comprising a sequence derived from a WEE genome or from WEE cDNA; a recombinant polynucleotide encoding an epitope of WEE; a recombinant vector containing any of the above recombinant polynucleotides, and a host cell transfected with any of these vectors.

Other aspects of the invention are: a purified VEE IE polynucleotide; a recombinant VEE IE polynucleotide; a recombinant polynucleotide comprising a sequence derived from a VEE IE genome or from VEE IE cDNA; a recombinant polynucleotide encoding an epitope of VEE IE; a recombinant vector containing any of the above recombinant polynucleotides, and a host cell transformed with any of these vectors.

In a further aspect of the invention is a complete sequence of the VEE subtype IIIA structural protein genes useful for diagnostics and vaccine development. Also provided is a chimeric virus containing the structural sequences of VEE IIIA, which is completely attenuated and provides protection against challenge with VEE IIIA virulent virus for use as a vaccine Another aspect of the invention is a single-stranded DNA sequence comprising a cDNA clone coding for an infectious WEE, the cDNA clone including at least one attenuating mutation therein, the RNA produced from transcription of the CDNA and the virus particles produced from the RNA in a host cell for use as a vaccine.

In another aspect of the invention there is provided a full length WEE cDNA clone containing a defined deletion mutation useful for attenuating the virus for the identification of suppressor mutations in the virus. The attenuated virus with the cleavage deletion and suppressor mutations are useful as a means to generate an attenuated, live WEE virus vaccine for veterinary and human use.

In a further aspect of the invention is provided a chimeric virus containing nonstructural protein gene sequences from WEE and structural protein gene sequences from any alphaviruses including but not limited to Aura, Barmah Forest, Bebaru, Cabassou, Chikungunya, eastern equine encephalitis, Everglades, Fort Morgan, Getah, Highlands J, Kyzylagach, Mayaro, Middelburg, Mucambo, Ndumu, O'nyong-nyong, Pixuna, Ross River, Sagiyama, Semliki Forest, SAAR87, Sindbis, Tonate, Una, Venezuelan equine encephalitis, Whataroa, which could be used as a means for attenuating virulent alphaviruses, and vaccine production against other alphaviruses.

Taking advantage of the close evolutionary relationship between WEE and eastern equine encephalitis virus (EEE), a chimeric virus has been constructed in which the structural protein genes of EEE have been inserted into the infectious clone in place of the WEE structural protein genes. The resulting virus is fully replication competent, attenuated, and elicits an immune response in mice which is protective against a lethal challenge with virulent EEE virus.

In addition, depending on the non-WEE sequences substituted for the WEE structural genes, another aspect of the invention includes a means for expressing antigens of other alphaviruses as chimeric alphaviruses for use as potential vaccines for human and veterinary use.

In another aspect of the invention there is provided a full length infectious VEE IE cDNA clone containing a cleavage deletion useful in the identification of suppressor mutations in the virus, the RNA produced from the cDNA and the virus produced from the RNA. The virus with the cleavage deletion and suppressor mutations is useful as a means to generate an attenuated, live VEE IE vaccine virus for veterinary and human use.

In a further aspect of the invention is provided a chimeric virus containing nonstructural sequences from VEE IE and structural sequences from other alphaviruses which could be used as a means of attenuating virulent alphaviruses.

In addition, depending on the non-VEE IE sequences substituted for the structural sequences of VEE IE, another aspect of the invention includes a means to express antigens of other alphaviruses as chimeric alphaviruses as potential vaccines for human and veterinary use.

In a further aspect of the invention, there is provided a vaccine protective against WEE, the vaccine comprising live attenuated WEE virus in an amount effective to elicit protective antibodies in an animal to WEE and a pharmaceutically acceptable diluent, carrier, or excipient.

In yet a further aspect of the invention, there is provided a vaccine protective against VEE IE, the vaccine comprising live attenuated VEE IE virus in an amount effective to elicit protective antibodies in an animal to VEE IE and a pharmaceutically acceptable diluent, carrier, or excipient.

In another aspect of the invention, there is provided a bivalent vaccine protective against WEE and VEE IE, the vaccine comprising both attenuated WEE and attenuated VEE IE in an amount effective to elicit protective antibodies in an animal to both WEE and VEE IE and a pharmaceutically acceptable diluent. In addition, it is possible that this vaccine will provide short lived protection against other alphaviruses (Cole and McKinney [1971] Inf. Immunity 4:37–43).

In yet another aspect of the invention, there is provided an inactivated vaccine produced from the live attenuated virus described above. The attenuated virus of the present invention whether whole virus or chimearic virus can be used in producing inactivated virus vaccines. By using an attenuated virus strain, there is a much greater margin of safety in the event that the produce is incompletely inactivated. Starting with an attenuated strain is also much safer during the manufacturing phase, and allows production under lower biocontainment levels.

BRIEF DESCRIPTION OF THE DRAWINGS

These and other features, aspects, and advantages of the present invention will become better understood with reference to the following description and appended clams, and accompanying drawings where.

DETAILED DESCRIPTION

Figure 1A:
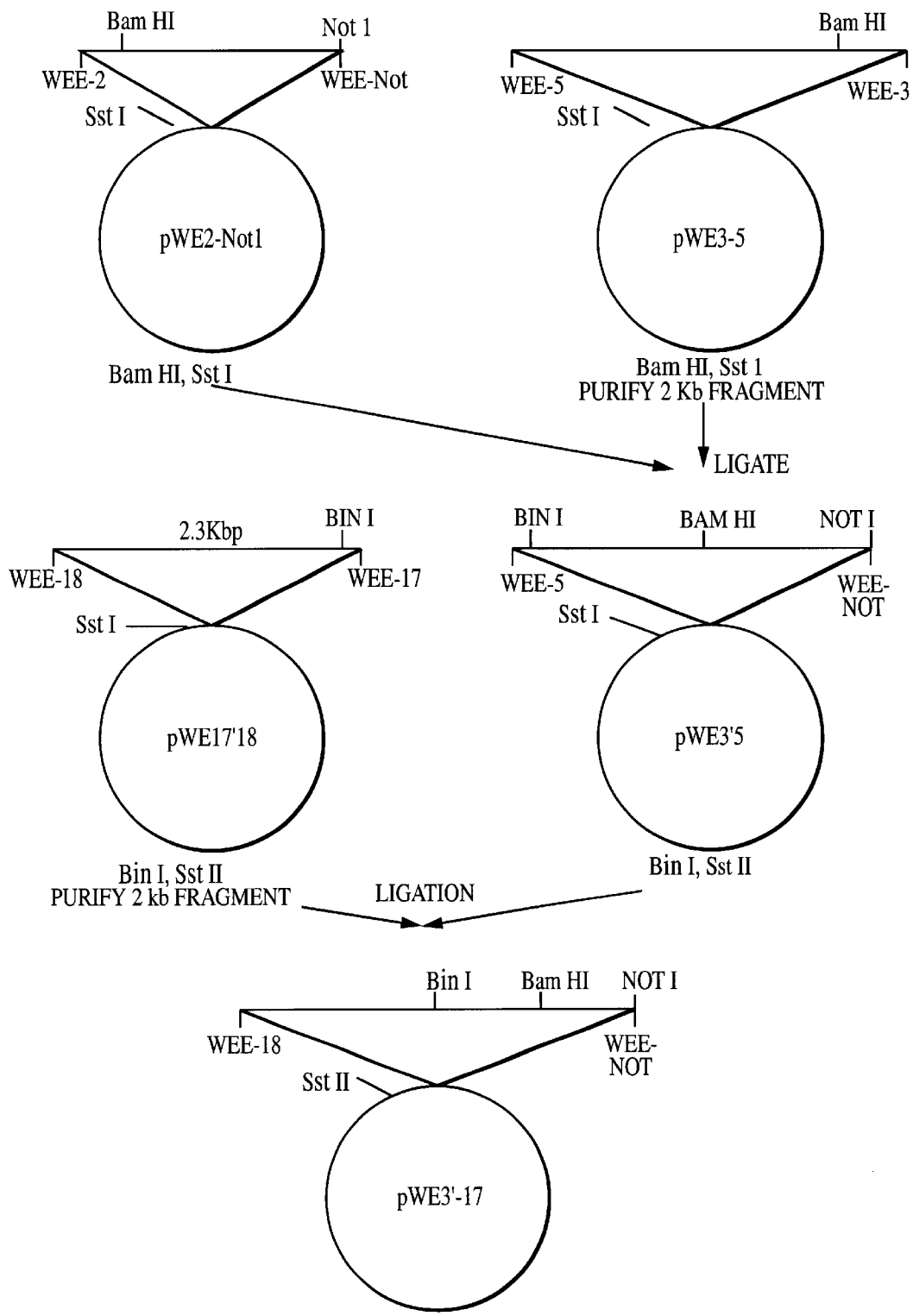
FIGS. 1A, 1B and 1C. Assembly of the full length cDNA clone of western equine encephalitis virus. Polymerase chain reaction products representing the entire genome of WEE virus were prepared with the primer pairs indicated. Each of the products was cloned into pBluescript KS+. Assembly of the full length clone, pWE2000 in pBluescript was carried out as indicated in the figure and described below. The clones are not drawn to scale. In each of the plasmids, the primers used to generate the PCR products are indicated as are the restriction endonuclease sites used for the assembly.

In one embodiment, the present invention relates to a full length cDNA clone of fully virulent WEE virus specified in SEQ ID NO:1, and a full length cDNA clone of fully virulent VEE IE variant specified in SEQ ID NO:2.

WEE, strain CBA/87, isolated from the brains of an infected horse in Argentina in 1987 (Bianchi et al., [1987] *Am. J. Trop. Med. Hyg.* 49:322–328) was used as a parent strain in the instant invention. Any other strain which consistently kills 100% of 5 week old C57BL6 mice when inoculated subcutaneously can be used such as B11, for example. The cDNA clone can be generated by any of a variety of standard methods known in the art. Preferably, DNA representing the entire genome can be prepared by polymerase chain reaction using a series of primer pairs based upon the partial genome sequences previously deposited in GenBank. The 5' terminal sequence of the virus may be determined by 5'-RACE basically as described by Frohman et al.([1988] *Proc. Natl. Acad. Sci. U.S.A.* 85:8998–9002). Assembly of the full length clone can be in a suitable transcription vector such as, for example, pBluescript KS+, using convenient restriction endonuclease sites or the entire genome could be inserted into any plasmid which contains suitable restriction endonuclease cleavage sites for cloning, an origin of replication so that the plasmid can be propagated in a bacterial host, and a selectable marker gene to maintain the plasmid in the bacterial cell during growth. The DNA sequence preferably has a complementary DNA sequence bonded thereto so that the double-stranded sequence will serve as an active template for RNA polymerase. Hence, the transcription vector preferably comprises a plasmid. When the DNA sequence comprises a plasmid, it is preferred that a unique restriction site be provided 3' (with respect to the virion RNA sequence) to ("down-stream" from) the cDNA clone. This provides a means for linearizing the DNA sequence to enhance the efficiency of transcription of genome-length RNA in vitro.

The complete clone is preferably operatively associated with a promoter region such that the promoter causes the cDNA clone to be transcribed in the presence of an RNA polymerase which binds to the promoter. The promoter is positioned on the 5' end (with respect to the virion RNA sequence), or upstream from, the cDNA clone. An excessive number of nucleotides between the promoter sequence and the cDNA clone will result in the inoperability of the construct. Hence, the number of nucleotides between the promoter sequence and the cDNA clone is preferably not more than eight, more preferably not more than than 5, still more preferably not more than 3, and most preferably not more than 1. Exemplary promoters useful in the present invention include, but are not limited to, T3 promoters, T7 promoters, and SP6 promoters. It is preferable that the 5' end of the in vitro transcript not have any additional nucleotides preceding the first nucleotide of the viral sequence. At the 3' end, additional nucleotides can be tolerated in the in vitro transcript but are probably lost when the virus replicates. In most instances, the poly-da tract at the 3' end is required for viability of the virus. Selection of the virulent full length clone can be achieved by comparing the $LD_{50}$ of the virus encoded by the cloned cDNA with the $LD_{50}$ of the parent virus used, in the instant example, WEE CBA/87. The ability to produce virulent virus is important; it allows the introduction and testing of attenuation mutations and the attenuated phenotype against a standard: the virulent parent.

Transfection of cells with the RNA transcript coded by the full length genomic cDNA can be achieved by any suitable means, such as, for example, by treating the cells with DEAE dextran, treating the cells with "LIPOFECTIN", and by electroporation. Togavirus-permissive cells, alphavirus-permissive cells, and WEE-permissive and VEE IE-permissive cells are cells which, upon transfection with the viral RNA transcript, are capable of producing viral particles. Togaviruses have a broad host range. Examples of such cells include, but are not limited to, Vero cells, baby hamster kidney cells, chicken embryo fibroblast cells, Chinese hamster ovary cells (CHO), mouse L cells, MRC-5 cells, mosquito cells such as C6–36 cells, to name a few.

In the case of VEE IE, an isolate of VEE IE, strain 68U201, was used. Any isolate known to cause disease in man can be chosen. In addition the ability of a strain to have an easily identifiable phenotype such as, for example, the ability to form large plaques in tissue culture on indicator cell monolayers, is helpful. In the present invention, the full length clone of VEE IE was obtained using oligonucleotide primers specific for the VEE IE strain 68U201 sequence. Reverse transcription-polymerase chain reaction (RT-PCR) of strain 68U201 viral RNA was carried out to generate numerous cDNA fragments that were subsequently cloned and used to assemble a full-length CDNA in a plasmid such that the cDNA could be precisely transcribed and viral infectious RNA produced. It is also possible to produce the entire genome by polymerase chain reaction by including the promoter sequence in the 5' end primer thereby producing infectious RNA directly from the PCR fragment. It is also possible to transcribe the viral RNA from a plasmid in the cell by transfection with the appropriate plasmid containing a promoter utilized by cellular RNA polymerases, i.e. the CMV promoter.

To determine virulence of the cloned viral genome, mice can be innoculated subcutaneously with $10^4$ plaque forming units of the cloned virus. The clone is considered virulent if all mice die, and not fully virulent if mice do not all die. The $LD_{50}$ of parent VEE IE strain 68U201 is to 1–2 pfu, therefore, if inoculation of 10,000-fold did not cause lethal disease in all mice, it was considered attenuated.

In another embodiment of the present invention is provided a cDNA sequence of the entire 26S region of VEE subtype IIIA as well as the structural protein genes specified in SEQ ID NO:3.

DNA or polynucleotide sequences to which the invention also relates include sequences of at least about 6 nucleotides, preferably at least about 8 nucleotides, more preferably at least about 10–12 nucleotides, most preferably at least about 15–20 nucleotides corresponding, i.e., homologous to or complementary to, a region of the WEE, VEE IE, or VEE IIIA nucleotide sequence. Preferably, the sequence of the region from which the polynucleotide is derived is homologous to or complementary to a sequence which is unique to the virus. Whether or not a sequence is unique to the virus can be determined by techniques known to those of skill in the art. For example, the sequence can be compared to sequences in databanks, e.g., GenBank. Regions from which typical DNA sequences may be derived include but are not limited to, for example, regions encoding specific epitopes, as well as non-translated regions.

The derived polynucleotide is not necessarily physically derived from the nucleotide sequence of the alphaviruses, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays and for the discovery of other alphavirus sequences.

A polypeptide or amino acid sequence derived from the amino acid sequence of alphavirus, refers to a polypeptide having an amino acid sequence identical to that of a polypeptide encoded in the sequence, or a portion thereof wherein the portion consists of at least 2–5 amino acids, and more preferably at least 8–10 amino acids, and even more preferably at least 11–15 amino acids, or which is immunologically identifiable with as a polypeptide encoded in the sequence.

A recombinant or derived polypeptide is not necessarily translated from a designated nucleic acid sequence, it may be generated in any manner, including for example, chemical synthesis, or expression of a recombinant expression system.

Once a complete viral genomic cDNA is cloned, attenuation of the virus is possible. An attenuating mutation refers to a nucleotide mutation or amino acid coded for in view of such a mutation which results in a decreased probability of causing disease in its host (i.e., a loss of virulence), in accordance with standard terminology in the art. The attenuating mutation may be a substitution mutation or an in-frame deletion mutation.

Novel WEE attenuating mutations disclosed herein which may be used to carry out the present invention include deletion of five amino acids at the furin cleavage site in combination with a substitution of lysine for glutamic acid at codon 182 at E2, or deletion of five amino acids at the furin cleavage site in combination with a subsitution of lysine for glutamic acid at codon 181 at E2. Additionally, certain mutations placed in the non-coding region at the 5' end of the genome have been found to be attenuating, specifically, a C to T change at nucleotide 7, an A to G change at nucleotide 13, a T to A change at nucleotide 25 and deletion of an A at nucleotide 22. These novel attenuating mutations may be inserted together in a cDNA clone encoding WEE virus resulting in an attenuated WEE which is reflected by 100% survival of mice inoculated by subcutaneous and intracranial routes. Such an attenuated live virus is immunogenic and protective against a lethal virus challenge.

Novel attenuating mutations can be discovered in the VEE IE by introducing mutations which are not reparable by the viral RNA replication process. A preferable mutation is the deletion of the four amino acids of the furin-like cleavage site between the E3 and E2 proteins. Transfection of the mutant viral genome into cells can result in the suppression of the lethal effect of the deletion mutation due to the error prone process of alphavirus replication. Once efficiently replicating viral progeny is generated they can be detected by plaque assays and analyzed for the presence of pE2 protein which indicates that the virus contains the deletion mutation. Attenuated but yet immunogenic virus with a cleavage deletion mutation and suppressor mutations) could be tested for its ability to protect animals from challenge with virulent VEE IE.

Attenuating mutations may be introduced into cDNAs encoding live WEE or VEE IE by any suitable means, such as site-directed mutagenesis (Please see e.g., Maniatis, Fritsch and Sambrook, *Molecular Clonina: A Laboratory Manual* (1982) or *DNA Cloning*, Volumes I and II (D. N. Glover ed. 1985) or *Current Protocols in Molecular Biology*, Ausubel, F. M et al. (Eds.) John Wiley & Sons, Inc., for general cloning methods.).

In another embodiment of the present invention is provided a chimeric virus containing nonstructural sequences from one alphavirus and structural sequences from other alphaviruses which could be used as a means of attenuating virulent alphaviruses. By "Structural sequences" as used herein is meant sequences encoding proteins which are required for encapsidation (e.g., packaging) of the viral genome, and include the capsid protein, E1 glycoprotein, and E2 glycoprotein. By "nonstructural sequences" is meant nonstructural protein sequences, or sequences which encode viral RNA polymerase(s) proteins. Viruses from which structural sequences can be used in the chimeric virus using WEE "nonstructural genes" as the backbone clone can include for example, all strains of WEE, EEE, and Sindbis, Aura, Barmah Forest, Bebaru, Bijou Bridge, Cabassou, Chikungunya, Everglades, Fort Morgan, Getah, Highlands J, Kyzylagach, Mayaro, Middelburg, Mucambo, Ndumu, O'nyong-nyong, Pixuna, Ross River, Sagiyama, Semliki Forest, SAAR87, Tonate, Una, Venezuelan Equine Encephalitis, Whataroa, to name a few. Acceptable structural protein genes would include a nucleocapsid protein capable of both packaging the chimeric viral genome and which can interact with the glycoproteins to initiate particle assembly. Chimearic virus is constructed by excision of the structural protein genes of the backbone virus and replacement with the desired structural protein genes from another virus. This can be accomplished in one of several ways. For example, site-directed mutagenesis can be used to excise the structural protein genes and leave a restriction endonuclease digestion site at the point of deletion. The structural protein genes of another alphavirus would then be cloned into that restriction site. Any virus obtained after transfection of cells with RNA transcribed from that clone would by definition be a chimeric virus.

In the case where the first and second viruses are closely related, another method can be used wherein cloned structural cDNA sequences of a second alphavirus can be digested at restriction enzyme sites which both viruses have in common. The cDNA fragments of the second virus can then be cloned into the homologous sites in the first virus structural protein locus such that the resulting structural protein genes of the chimeric are a composite of both. Other methods for producing a chimearic virus are known to people in the art (Kuhn et al. [1996] *J. Virology* 70:7900–7909).

In another embodiment, the attenuated viruses of the present of invention can be used to prepare replicon expression systems. A replicon expression system consists of three components. The first is a replicon which is equivalent to a full length infectious clone from which all of the viral structural proteins have been deleted. A multiple cloning site can be cloned into the site previously occupied by the structural protein genes. Virtually any heterologous gene may be cloned into this cloning site. Transcription of RNA from the replicon yields an RNA capable of initiating infection of the cell identically to that seen with the full-length infectious virus clone. However, in lieu of the viral structural proteins, the heterologous antigen is expressed. This system does not yield any progeny virus particles because there are no viral structural proteins available to package the RNA into particles.

Particles which appear structurally identical to virus particles can be produced by supplying structural proteins for packaging of the replicon RNA in trans. This is typically done with two helpers. One helper consists of a full length infectious clone from which the nonstructural protein genes and the glycoprotein genes are deleted. The helper retains only the terminal nucleotide sequences, the promoter for subgenomic mRNA transcription and the sequence for the viral nucleocapsid protein. The second helper is identical to the first except that the nucleocapsid gene is deleted and only the glycoprotein genes are retained. The helper RNA's are transcribed in vitro and co-transfected with replicon RNA. Because the replicon RNA retains the sequences for packaging by the nucleocapsid protein, and because the helpers lack these sequences, only the replicon RNA is packaged by the viral structural proteins and released from the cell. The particles can then be inoculated into animals similar to parent virus. The replicon particles will initiate only a single round of replication because the helpers are absent, they produce no progeny virus particles, and express only the viral nonstructural proteins and the product of the heterologous gene cloned in place of the structural proteins. The heterologous gene product is then detected by the host immune system and appropriate immune response is then mounted.

The WEE and VEE IE replicons can be used to express heterologous genes of interest as well as a means for expressing antigens or immunogenic proteins and peptides of interest, in vitro or in vivo. The immunogenic protein or peptide, or "immunogen" may be any immunogen suitable for inducing an immune response protective against a pathogen from which the immunogen is derived, including but not limited to microbial, bacterial, protozoal, parasitic, and viral pathogens. For example, the immunogen can be the expression product of any heterologous gene of interest, including influenza hemagglutinin, lassa fever nucleocapsid and glycoproteins, portions of bacterial toxin genes, HIV glycoprotein, Ebola glycoprotein, to name a few.

In yet another embodiment, the present invention provides inactivated virus vaccines produced from live attenuated virus preparations, either as virus with attenuating mutations as has been described for WEE and VEE IE or chimeric viruses described above for EEE and VEE IIIA. The inactivation of live virus is well known in the art and can be performed, for example, by the use of formalin. Inactivated attenuated virus vaccine has a greater safety margin both as a final vaccine in case of incomplete inactivation, and during the manufacturing process allowing production under lower biocontainment levels.

Subjects which may be administered the live attenuated or inactivated attenuated viruses and vaccine formulations disclosed herein include both humans and animals (e.g. horse, donkey, pigs, mice, hamster, monkey, birds).

Vaccine formulations of the present invention comprise an immunogenic amount of a live attenuated virus, or a combination of live attenuated viruses as a multivalent vaccine, as disclosed herein in combination with a pharmaceutically acceptable carrier. An "immunogenic amount" is an amount of the attenuated virus sufficient to evoke an immune response, particularly an immune response to the protein or peptide encoded by the heterologous RNA carried by the virus, in the subject to which the virus is administered. An amount of from about $10^1$ to $10^5$ plaque forming units of the live virus per dose is suitable, depending upon the age and species of the subject being treated. Exemplary pharmaceutically acceptable carriers include, but are not limited to, sterile pyrogen-free water and sterile pyrogen-free physiological saline solution.

Administration of the live attenuated viruses disclosed herein may be carried out by any suitable means, including both parenteral injection (such as intraperitoneal, subcutaneous, or intramuscular injection), by in ovo injection in birds, and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed.

In another embodiment, the present invention relates to antibodies specific for the above-described virus. For instance, an antibody can be raised against any of the viral proteins or against a portion thereof. Persons with ordinary skill in the art using standard methodology can raise monoclonal and polyclonal antibodies to a polypeptide of the present invention. Material and methods for producing antibodies are well known in the art (see for example Goding, in, *Monoclonal Antibodies: Principles and Practice*, Chapter 4, 1986). The antibodies can be used to monitor the presence or activity of alphaviruses and potentially as a therapeutic agent.

In a further embodiment, the present invention relates to a method of detecting the presence of WEE, EEE, VEE IIIA or VEE IE viral infection or antibodies against these viruses, if present, in a sample. Using standard methodology well known in the art, a diagnostic assay can be constructed by coating on a surface (i.e. a solid support) for example, a microtitration plate or a membrane (e.g. nitrocellulose membrane), all or a unique portion of WEE, EEE, VEE IIIA or VEE IE virus described above, and contacting it with the serum of a person suspected of having a viral infection. The presence of a resulting complex formed between the virus and antibodies specific therefor in the serum can be detected by any of the known methods common in the art, such as colorimetry or microscopy. This method of detection can be used, for example, for the diagnosis of WEE, EEE, VEE IIIA and VEE IE viral infections.

In yet another embodiment, the present invention relates to a method of detecting the presence of WEE, EEE, VEE IIIA or VEE IE viruses in a sample. Using standard methodology well known in the art, a diagnostic assay can be constructed by coating on a surface (i.e. a solid support) for example, a microtitration plate or a membrane (e.g. nitrocellulose membrane), antibodies specific for WEE and/or VEE IE, and contacting it with serum or tissue sample of a person suspected of having a WEE or VEE IE viral infection. The presence of a resulting complex formed between virus in the serum and antibodies specific therefor can be detected by any of the known methods common in the art, such as fluorescent antibody spectroscopy or colorimetry. This method of detection can be used, for example, for the diagnosis of WEE, EEE, VEE IIIA and VEE IE viral infection.

In another embodiment, the present invention relates to a diagnostic kit which contains WEE, EEE, VEE IE, or VEE IIIA virus and ancillary reagents that are well known in the art and that are suitable for use in detecting the presence of antibodies to WEE and VEE IE in serum or a tissue sample. Tissue samples contemplated can be obtained from birds, monkey, human, or other mammals.

In yet a further embodiment, the present invention relates to DNA or nucleotide sequences for use in detecting the presence or absence of WEE, EEE, VEE IE or VEE IIIA virus using the reverse transcription-polymerase chain reaction (RT-PCR). The DNA sequence of the present invention can be used to design primers which specifically bind to the viral RNA for the purpose of detecting the presence, absence, or quantitating the amount of virus. The primers can be any length ranging from 7–40 nucleotides, preferably 10–15 nucleotides, most preferably 18–25 nucleotides. Reagents and controls necessary for PCR reactions are well known in the art. The amplified products can then be analyzed for the presence or absence of viral sequences, for example by gel fractionation, with or without hyridization, by radiochemistry, and immunochemical techniques.

In yet another embodiment, the present invention relates to a diagnostic kit which contains PCR primers specific for WEE, EEE, VEE IE or VEE IIIA and ancillary reagents that are well known in the art and that are suitable for use in detecting the presence or absence of WEE, EEE, VEE IE or VEE IIIA in a sample using PCR. Samples contemplated can be obtained from birds, human, or other mammals.

In another embodiment, the present invention relates to a method of reducing WEE, EEE, VEE IE, or VEE IIIA viral infection symptoms in a patient by administering to said patient an effective amount of anti WEE, anti EEE, anti VEE IE, or anti VEE IIIA antibodies, or protective serum from an immunized animal. When providing a patient with antibodies, the dosage of administered agent will vary depending upon such factors as the patient's age, weight, height, sex, general medical condition, previous medical history, etc. In general, it is desirable to provide the recipient with a dosage of the above compounds which is in the range of from about 1 pg/kg to 10 mg/kg body weight of patient, although a lower or higher dosage may be administered.

In another embodiment, the present invention relates to a method for overcoming vaccine interference in alphavirus-immune individuals. Alphavirus interference has been documented in animals and people since the 1960's. This phenomenon occurs when a live-attenuated vaccine is administered to animals or people with existing immunity to heterologous alphaviruses. Pre-existing immunity may be acquired by vaccination or infection. This presents a significant limitation to the usefulness of the current live-attenuated alphavirus vaccines, especially since the cross-reactive immunity does not protect adequately against challenge with virulent heterologous alphaviruses. Formalin-inactivated vaccines are not an acceptable alternative as they have significant limitations with regard to the quality and duration of protective immunity and require multiple inoculations and periodic boosters. The attenuated WEE, EEE, VEE IIIA and VEE IE virus vaccines of the present invention contain mutations in the viral glycoprotein sequences that may alter the sequence, conformation, and/or accessibility of cross-reactive epitopes. Alterations in epitopes that prevent binding by cross-reactive antibodies may also bypass interference in alphavirus-immune individuals. Eliminating the problem of interference would permit the WEE and VEE IE attenuated virus vaccines to be used in alphavirus-immune animals or people to induce protective immunity to western equine encephalitis virus and/or to Venezuelan equine encephalitis virus variant IE. Long-lasting protective immunity to both parenteral and aerosol challenge would be expected after vaccination with the live-attenuated vaccines of the present invention, and provide an additional advantage over the use of inactivated vaccines which induce short-lived responses that do not protect against mucosal challenge.

Having now described the invention, the following examples are provided to illustrate the present invention, and should not be construed as limiting thereof. In light of the present disclosure, numerous embodiments within the scope of the claims will be apparent to those of ordinary skill in the art.

Attenuated WEE

The following materials and methods were used in the examples that follow.

Viruses and cells. Western equine encephalitis virus, strain CBA/87 (Bianchi et al. 1988) and eastern equine encephalitis virus, strain Fla91-4679 (Mitchell et al. [1992] *Science* 257:526–7) were grown in BHK cells in EMEM containing 10% fetal bovine serum, 100 U/ml penicillin G and 100 μg/ml streptomycin. Primary chicken embryo fibroblasts were grown in EMEM containing 5% fetal bovine serum. Baby hamster kidney cells and Vero cells were grown in EMEM containing 10% fetal bovine serum.

cDNA cloning. Genomic RNA was prepared from purified virus by phenol:chloroform extraction and ethanol precipitation. Initially, cDNA was prepared by the method of Gubler and Hoffman ([1983] *Proc. Natl. Acad. Sci. U.S.A.* 85:5997–6001). Subsequently, DNA representing the entire genome was prepared by polymerase chain reaction using a series of primer pairs (Table 1, FIG. 1) based upon the partial genome sequences previously deposited in GenBank. Each PCR product was cloned into pCRII (Invitrogen). The 5' terminal sequence of CBA/87 virus was determined by 5'-RACE basically as described by Frohman et al. ([1988] *Proc. Natl. Acad. Sci. U.S.A.* 85:8998–9002). The oligonucleotide, CBA/87 5', consisted of an SstII site, the promoter for bacteriophage T7 RNA polymerase followed by one G and 14 nucleotides of the 5' terminus of CBA/87 terminal sequence was paired with ns1962 and used to amplify the terminal 1.9 kb of the WEE genome. Clone pWE2000 representing the entire genome was assembled in pBluescript KS+ through the use of convenient restriction endonuclease sites.

TABLE 1

Oligonucleotide Primers for Preparation of WEE PCR Products

| | |
|---|---|
| CBA/87 -T7-Sst2 | GTCACCGCGGTAATACGACTCACTATAGATAGGGCATGGTATAGAG (SEQ ID NO: 4) |
| NS1962 | TCACCTTATTCTGGAACACATCAG (SEQ ID NO: 5) |
| WEE-7 | TCGGAGGAAGGCTGATGAAAC (SEQ ID NO: 6) |

TABLE 1-continued

Oligonucleotide Primers for Preparation of WEE PCR Products

| | | |
|---|---|---|
| WEE-10 | TCGGATCCGATGAGAAAATATACGCTCCC (SEQ ID NO: 7) | |
| WEE-17 | GACTGGATCCGCAAACCAGTCCTGTTCTCAGG | (SEQ ID NO: 8) |
| WEE-18 | GCATGGATCCAGCATGATCGGAAATGTCTTGTC | (SEQ ID NO: 9) |
| WEE-5 | TCGGATCCACCGCCAAAATGTTTCCATAC (SEQ ID NO: 10) | |
| WEE-3 | TCGGGATCCCCGGAACATTTGGC (SEQ ID NO: 11) | |
| WEE-2 | CTGCTTTTCATGCTGCATGCC (SEQ ID NO: 12) | |
| WEE-Not | CGATGCGGCCGCTTTTTTTTTTTTTTTTGAAATTTTAAAAAC | (SEQ ID NO: 13) |
| WEE-CL2 | CAGCGTGAAGTCATCGGTAATGCTGCGTGATGGACATTTCAAG | (SEQ ID NO: 14) |
| WEE-CL1 | CAGCGTGAAGTCATCGGTAATGCTTGATGGACATTTCAAG | (SEQ ID NO: 15) |

For ease of subsequent site-directed mutagenesis of the structural protein genes, two cassettes representing the 5' terminal 7.6 kb, plasmid pWE5'-18, and 3'4.2 kb, plasmid pWE3'-17, of the genome were prepared. Full length clones were assembled by digestion of the pWE5'-18 with BlnI and NotI and insertion of a 4.1 kb BlnI-NotI fragment prepared from the plasmid pWE3'-17 or its mutagenized derivatives.

A cassette containing the structural genes of eastern equine encephalitis virus strain Fla91-4679 was prepared by RT-PCR. The cassette was digested with BlnI and NotI and the 4.0 kb fragment was ligated to pWE5'-18 which had been similarly digested. The resulting plasmid was designated pMWE-7.

Mutaaenesis of the furin cleavaae site. Two oligonucleotides, WEE-CL2 and WEE-CL which bracket the presumed furin cleavage site, RRPKR, between the E3 and E2 glycporoteins were used to delete the 5 and 4 codons, respectively. Plasmid pWE3'-17 was used as template for mutagenesis. WEECL2 and WEECL were paired with primer WEE-5 to generate PCR products of 1.4 kb. The PCR products were purified and paired with WEE-3 for 10 cycles of PCR utilizing WE3'-17 as template. Additional WEE-5 primer was added to 500 nM and PCR was carried out for an additional 20 cycles. The 2.3 kb products were purified, digested with BstEII and NcoI and ligated into plasmid pWE3'-17 which had been digested with BstEII and NcoI. Clones containing the mutation were identified by loss of the NgoM1 site in the sequences encoding the furin cleavage site. The sequences of the mutations were confirmed by sequencing and the mutagenized pWE3'-17 cassettes were ligated to pWE5'-18 as described above to yield full length clones pWE2200 and pWE2100, respectively.

Identification of secondary mutations in virus derived from pWE2100 and pWE2200. Virus released from cells electroporated with RNA transcribed from pWE2200 were plaque-purified and grown into stock preparations. Supernatant from cells transfected with RNA transcribed from pWE2100 was diluted 10-fold and inoculated onto BHK cells. The supernatant was collected 48 hours later and the RNA was extracted directly from the culture fluid. For each mutant virus and the parent CBA/87 virus, viral RNA was extracted with Trizol LS (Life Technologies, Inc., Gaithersburg, Md.) and the glycoprotein genes of each were amplified by reverse transcription-polymerase chain reaction amplification. The PCR products were purified (PCR Prep, Promega Inc., Madison, Wis.) and sequenced on an ABI 373 sequencer using fluorescent-tagged terminators.

Transcription and transfection. Purified plasmid was digested with NotI, phenol extracted and ethanol precipitated. Typically 0.5–1 ug of linearized DNA was transcribed in vitro by T7 RNA polymerase (Ribomax, Promega, Madison, Wis.) in the presence of 3 mM m7GpppGp (Pharmacia, Piscataway, N.J.). Electroporation of BHK or CEF cells with 0.4 ug of RNA was done as described (Liljestrom et al. [1991] Bio/Technology 9:1356–1361). The cells were then seeded into T-75 flasks with 20 ml of medium and observed for cytopathology at 24 and 36 hours after electroporation. Virus was harvested when the cells displayed significant cytopathology and approximately 50% were detached from the plastic. Virus titers were determined by plaque assay on Vero and BHK cells.

EXAMPLE 1

Preparation of an Infectious Clone of WEE Strain CBA/87

Figure 1B:
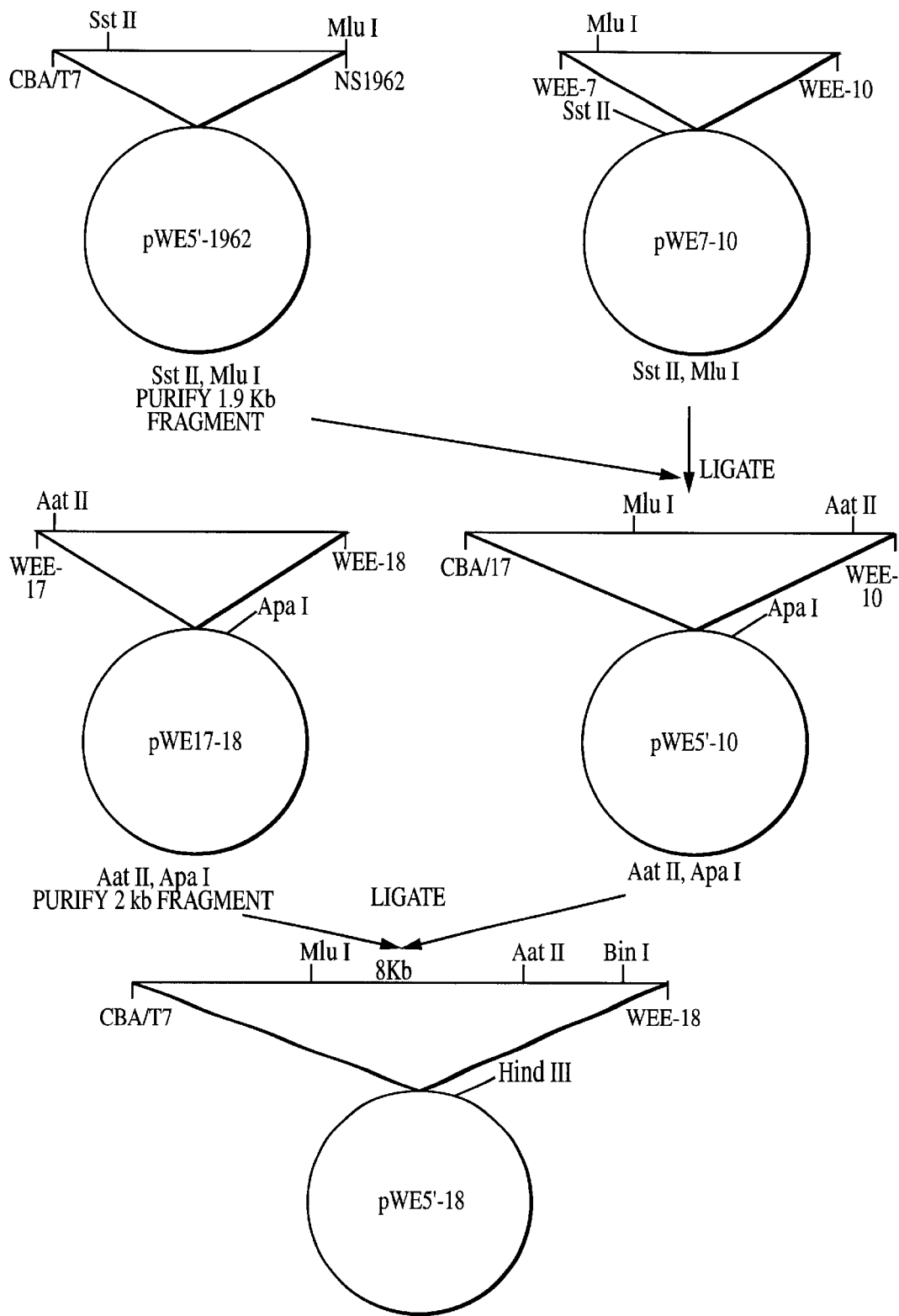
Figure 1C:
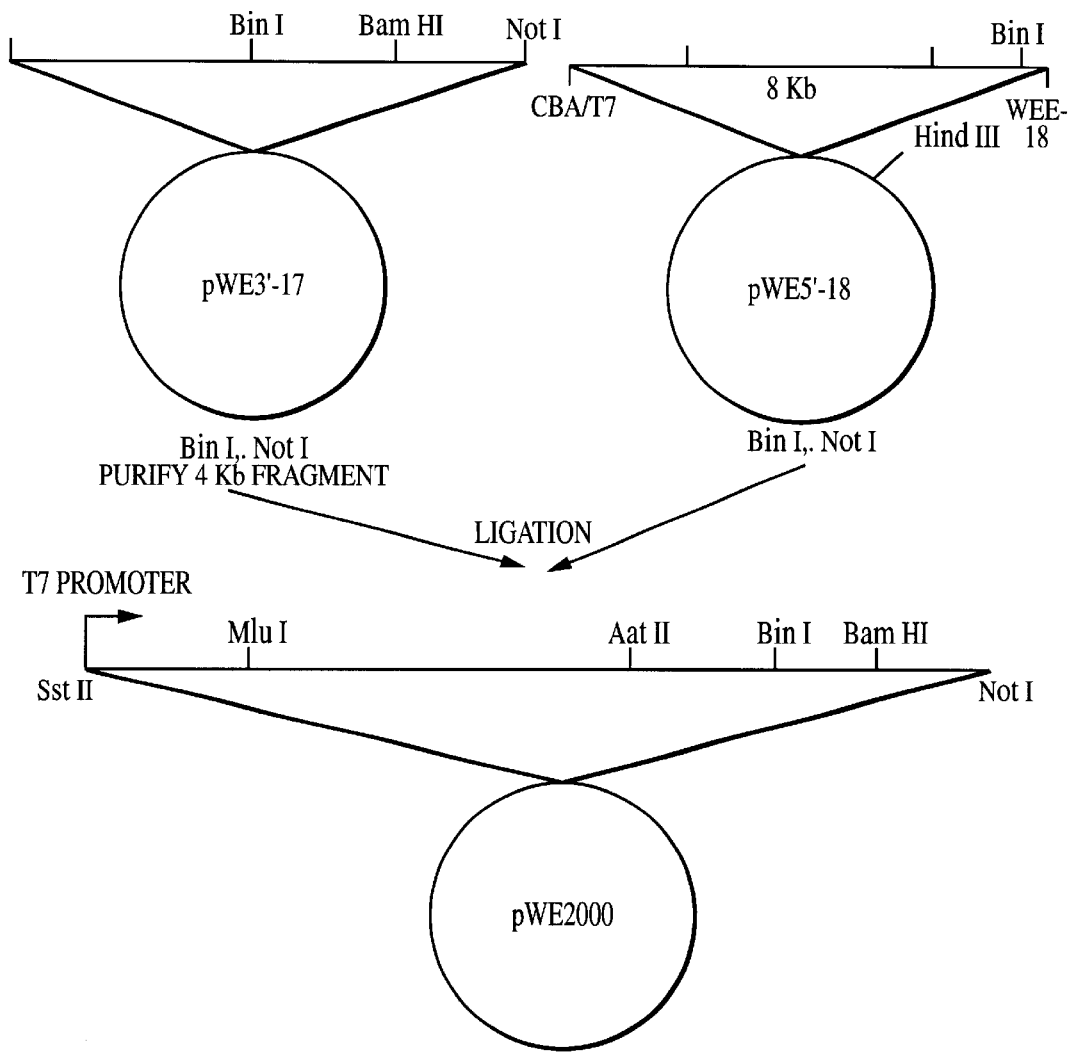

One goal of this study was to prepare a full length cDNA clone of fully virulent WEE virus such that mutations leading to an attenuated phenotype could be identified. WEE, strain CBA/87, isolated from the brain of an infected horse in Argentina in 1987 (Bianchi et al. [1988] Am. J. Trop. Med. Hyg. 49:322–328), was chosen as the parent virus as it consistently kills 100% of 5 week old C57BL6 mice when inoculated subcutaneously, allowing development of a convenient animal model to assess the relative effects on virulence of the attenuating mutations. Portions of the sequence of several strains of WEE virus had been determined previously and were used as a basis for primers to prepare amplification products representing the entire genome of the CBA/87 which were cloned in pCRII. Full length clones were assembled in pBluescript KS+ using convenient restriction sites as shown in FIG. 1. The first infectious clone pWE1000, contained the 5' terminal 20 nucleotides from eastern equine encephalitis virus. This clone produced viable virus which was highly attenuated exhibiting an subcutaneous LD $_{50}$ in mice of approximately $1.2 \times 10^6$ PFU compared to the CBA/87 parent virus where $LD_{50}$ was approximately 22.

A second clone with an authentic WEE 5'-terminus, pWE2000, was used for all subsequent experiments. Transfection of CEF or BHK cells with RNA transcribed from pWE2000 resulted in complete destruction of the monolayers within 36 hours and titers $>10^8$ PFU/ml were obtained by infection of either cell type with the resulting virus. Subcutaneous inoculation of 5 week old C57/Bl6 mice with WE2000 results in death within 9 days and the $LD_{50}$ of 75 PFU is only slightly higher than the $LD_{50}$ of 22 PFU of CBA/87 parent virus, Table 2. It should be noted that animals surviving the lower doses of virus challenge gave no serological evidence of infection. This level of virulence for WE2000 virus was considered sufficient to allow for further characterization of the mutations necessary for attenuation of the virus.

TABLE 2

C57 Black/6 Mice Inoculated Subcutaneously
with CBA/87 Parental virus and WE2000 Recombinant
Virus

| Virus Strain Dose | Mortality | Mean Day to Death (Days) | Prechallenge ELISA | Challenge (S/T) |
|---|---|---|---|---|
| CBA/87 | | | | |
| $3 \times 10^5$ | 10/10 | 8.4 | — | |
| $3 \times 10^4$ | 10/10 | 8.9 | — | |
| $3 \times 10^3$ | 10/10 | 9.2 | — | |
| $3 \times 10^2$ | 7/10 | 9.9 | <100 | 0/3 |
| $3 \times 10^1$ | 3/10 | 10 | <100 | 0/7 |
| 3 | 0/10 | — | <100 | 0/10 |
| WE2000 | | | | |
| $1 \times 10^7$ | 10/10 | 8.7 | — | — |
| $1 \times 10^6$ | 10/10 | 9.0 | — | — |
| $1 \times 10^5$ | 10/10 | 9.2 | — | — |
| $1 \times 10^4$ | 10/10 | 9.3 | — | — |
| $1 \times 10^3$ | 9/10 | 10.0 | <100 | 0/1 |
| $1 \times 10^2$ | 3/10 | 10.0 | <100 | 0/7 |
| $1 \times 10^1$ | 0/10 | — | <100 | 0/10 |
| 1 | 0/10 | — | <100 | 0/10 |

EXAMPLE 2

Preparation of Cleavage Mutants of CBA/87

Davis et al.([1995] *Virology* 212:102–110) have demonstrated that deletion of the furin cleavage site between E3 and E2 glycoproteins of VEE virus is a lethal mutation. However, prolonged incubation of cells which had been transfected with RNA derived from full length clones with the deletion, resulted in the eventual appearance of virus which was replication-competent and attenuated in mice (Davis et al., 1995, supra). Based upon a comparison of the predicted structural protein sequences of WEE and VEE, the probable cleavage site of CBA/87 virus is RRPKR. The presence of the extra arginine when compared to the conscensus (RX(R/K)R) alphavirus cleavage site indicated that the cleavage site of WEE virus might be more complex than that observed with VEE virus. We therefore, prepared two different deletion mutations in the E3-E2 cleavage site of the pWE2000 clone, pWE2100 which lacks five amino acids, RRPKR, and pWE2200 which lacks four amino acids, RPKR.

Development of CPE in cells after electroporation of RNA transcribed from pWE2100 and pWE2200 was delayed for 48 to 72 hours compared with pWE2000. In two instances, pWE2100 did not induce significant CPE in the transfected cells despite the fact that approximately $10^6$ PFU/ml were released into the medium of transfected cells. When assayed by plaque formation on Vero cells, both supernatants yielded extremely small plaques after 72 hours which never increased beyond 2 mm in diameter. In contrast, pWE2000 virus yields large plaques after 48 hours which enlarge to approximately 1 cm after 5 days under a 0.5% agarose overlay. The small plaque phenotype of the mutant viruses is stable after 3 passages in Vero or BHK cells, which is the limit to the passage of the virus used in these experiments.

Figure 2:
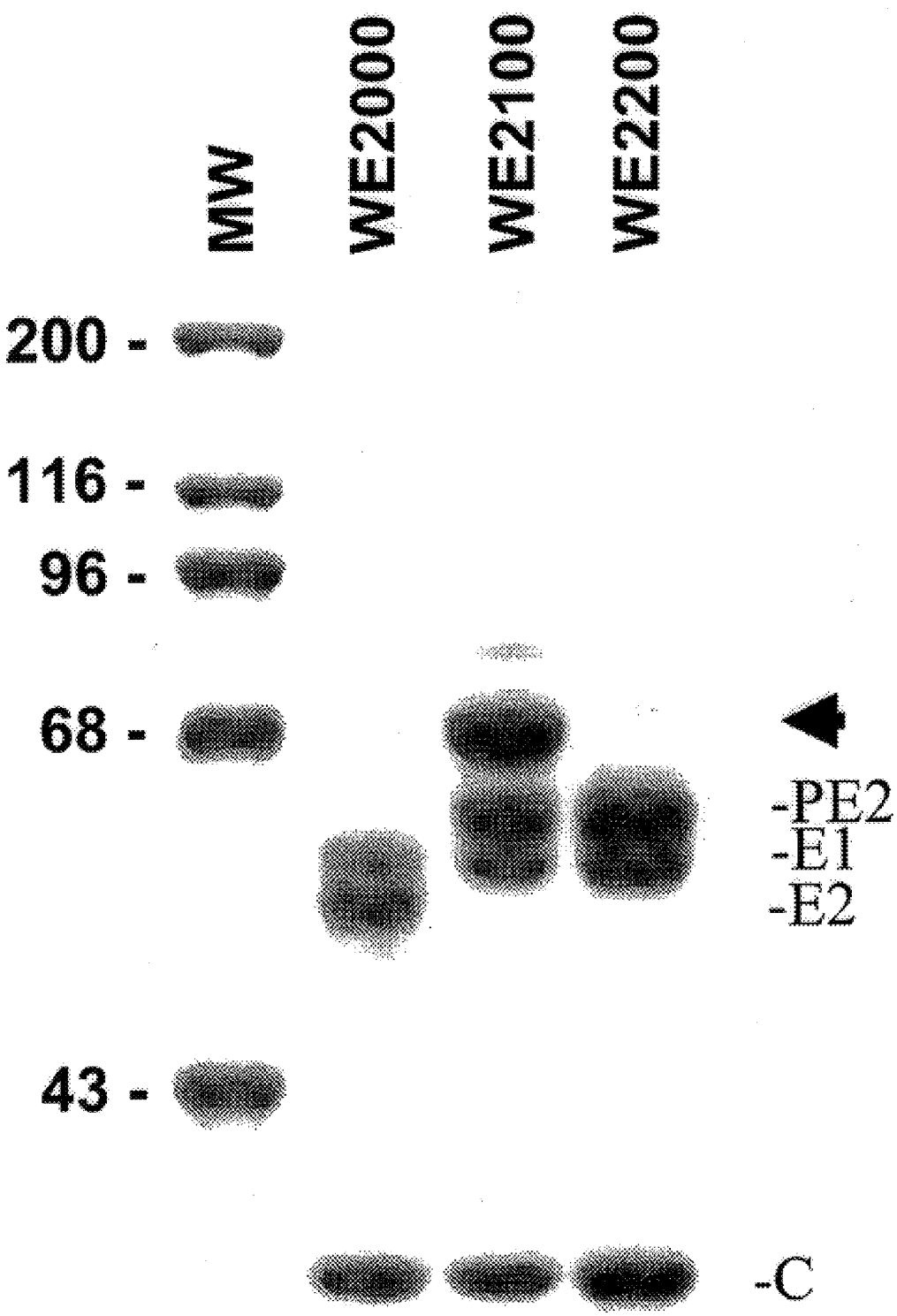
FIG. 2. Polypeptide profiles of western equine encephalitis viruses. Samples of purified virus were analyzed by electrophoresis on 10% polyacrylamide gels and stained with Comassie Brilliant blue. Molecular weight maker (MW) are shown in the first lane and molecular weights are indicated in daltons X $10^{-3}$. The virus strain is designated above the appropriate lane. Position of contaminating bovine serum albumin is indicated by arrow.

Analysis of the structural proteins of the WE2100 and WE2200 viruses by SDS-PAGE (FIG. 2) shows that in each instance, the deletions at the cleavage site result in a virus which lacks E2 protein and contains a larger protein, presumably pE2, indicating that deletion of the presumed cleavage site eliminated cleavage at this site.

The lack of rapid cytopathology after transfection of BHK cells with transcripts of pWE2200 and pWE2100 suggested that the mutants were non-viable and that the infectious virus subsequently detected by plaque assay was due to secondary mutations arising during the replication of the RNA as reported previously for deletion mutants of VEE (Davis et al., 1995, supra).

Three plaque isolates from WE2200 virus were chosen for further characterization. All isolates grew to high titer and exhibited a small plaque phenotype. The isolates were sequenced over the entire glycoprotein reading frame. As shown in Table 3, isolates 2215 and 2220 have a mutation of Glu to Lys at position 181 of the E2 glycoprotein. Strain WE2219 carries a single Glu to Lys at position 182 of the E2 protein. Strain WE2215 also has a conservative Val to Ala change at position 211 of the E2 glycoprotein. WE2220 has a Glu to Gly change at position 2 of the E1 glycoprotein and a Phe to Ser change at position 382 of the E1 glycoprotein.

TABLE 3

Genotypes of Recombinant WEE Virus Strains

| Virus[1] | Cleavage Site | E2[2] | E1[2] |
|---|---|---|---|
| CBA/87 | RRPKR | P(102), E(181), E(182) | E(2), F(257), P(382) |
| vWE2100 | ------ | K(182) | |
| pWE2102 | ------ | K(182) | |
| vWE2215 | R----- | K(181), A(211) | |
| vWE2219 | R----- | K(182) | |
| vWE2220 | R----- | K(181) | G(2), S(382) |

[1]p indicates viruses prepared by mutagenesis of infectious clones.
[2]Amino acid at position indicated in parenthesis.

In order to determine a consensus of the mutations appearing in virus produced from the pWE2100 RNA, the sequences of the glycoprotein genes were determined directly from cDNA prepared by RT-PCR of the genomic RNA extracted from virus released from BHK cells infected with virus released from the transfected cells. Sequence analysis of glycoprotein genes of WE2100 virus from the transfection supernatant revealed only two mutations. As seen previously in WE2219, WE2100 also had a Glu to Lys change at position 182 of the E2 glycoprotein (Table 3).

In order to determine which of the mutations identified in virus released from cells transfected with RNA transcripts from pWE2200 and pWE2100 served as the suppressor of the lethal effect of the cleavage deletion mutation, the mutations were individually placed into the pWE2200 and pWE2100 clones by site-directed mutagenesis. As shown in Table 4, three subclones of WE2200 were produced, and based upon the ability to induce CPE in BHK cells, it was demonstrated that the Glu to Lys change at position 181 of the E2 glycoprotein was necessary and sufficient to restore the ability of the WE2200 clone to encode replication competent virus. Similarly, placement of the Glu to Lys change at position 182 of the E2 glycoprotein was also sufficient to restore the ability of the WE2100 clone to encode replication competent virus. When the Glu to Lys changes at E2 position 181 or 182 were inserted into the parental infectious clone pWE2000, the resulting virus exhibited a small plaque phenotype on Vero cells as noted for each of the cleavage deletion mutants.

TABLE 4

Effect of site-directed mutagenesis on restoration of cytopathogenicity of pWE2200 and pWE2100

| Strain | Cleavage site | E2 | E1 | Viability |
|---|---|---|---|---|
| pWE2000 | RRPKR | | | Yes |
| pWE2200 | R---- | | | No |
| pWE2221 | R---- | | G(2) | No |
| pWE2222 | R---- | K(181) | G(2) | Yes |
| pWE2223 | R---- | K(181) | | Yes |
| pWE2100 | ----- | | | No |
| pWE2102 | ----- | K(182) | | Yes |

Although the cleavage deletion mutations in pWE2200 and pWE2100 differed by a single amino acid, the results indicate that the mutations at E2 residues 181 and 182 are both capable of restoring viability of the virus and appear to be equivalent.

EXAMPLE 3

Attenuation of WE2000 Virus

C57/BL6 mice are uniformly susceptible to lethal challenge by western equine encephalitis virus until approximately 9 weeks of age. Subcutaneous inoculation of five- or eight-week-old C57/BL6 female mice with CBA/87 or WE2000 viruses routinely results in lethal encephalitis after 8–9 days (Table 2). As noted previously, the WE2000 is slightly less virulent than the CBA/87 parent. The virulence of the progeny virus derived from pWE2100 and pWE2200 infectious clones were determined by subcutaneous inoculation of C57BL6 mice. In each instance, the viruses were significantly attenuated compared to virus produced from parent WE2000 clone. However, infection of mice with increasing doses of WE2215, WE2219 or WE2220, resulted in sporadic deaths with slightly extended periods prior to death compared to the parental virus (Table 5). These results indicated that deletion of only four amino acids from the cleavage site was inadequately attenuating, unlike the results obtained with VEE virus by Davis et al. (1995) and the viruses derived from WE2200 were not characterized further.

TABLE 5

C57BL6 Mice Inoculated Subcutaneously with WE2200 Cleavage Deletion Mutants

| Virus Strain Dose | Mortaliy | Mean day to Death | Prechallenge ELISA | Neut | Challenge | Post Challenge ELISA | Neut |
|---|---|---|---|---|---|---|---|
| CBA/87 | | | | | | | |
| $10^3$ | 10/10 | 9.1 | | | | | |
| $10^5$ | 10/10 | 7.7 | | | | | |
| WE2000 | | | | | | | |
| $10^3$ | 10/10 | 9.2 | | | | | |
| $10^5$ | 10/10 | 9.1 | | | | | |
| WE2215 | | | | | | | |
| $10^3$ | 1/10 | 12 | 504 (3/9) 100 (6/9) | <20(9/9) | 8/9 | 8300 | 761 |
| $10^5$ | 1/10 | 14 | 253 (7/9) 100 (2/2) | <20(9/9) | 9/9 | 12800 | 403 |
| WE2219 | | | | | | | |
| $10^3$ | 0/10 | — | 283 (2/8) 100 (6/8) | <20 (10/10) | 6/10 | 14368 | 2281 |
| $10^5$ | 2/10 | 12 | 200 (4/8) 100 (4/8) | <20(8/8) | 8/8 | 11738 | 1522 |
| WE2220 | | | | | | | |
| $10^3$ | 1/10 | 11 | 606 (5/9) 100 (4/9) | 20(3/9) <20 (6/9) | 5/9 | 14703 | 1280 |
| $10^5$ | 2/10 | 14 | 800 (7/8) 100 (1/8) | 20 (2/8) <20 (6/8) | 8/8 | 9051 | 761 |

When C57BL6 mice were inoculated subcutaneously with the uncloned WE2100 progeny virus, there were no deaths at any dilution, even at doses of $10^7$ PFU per mouse (Table 6). However, some of those mice inoculated subcutaneously with $10^5$ PFU or less remained susceptible to a lethal challenge with the virulent CBA/87 virus.

TABLE 6

C57 Black/6 Mice Inoculated Subcutaneously with WEE Virus Strain WE2100

| Virus strain Dose | Mortality[1] (%) | Mean Day to Death | Challenge[2] (%) |
|---|---|---|---|
| WE2100 | | | |
| $10^3$ | 0/10 (0) | — | 4/10 (40) |
| $10^4$ | 0/10 (0) | — | 7/10 (70) |
| $10^5$ | 0/10 (0) | — | 8/10 (80) |
| $10^6$ | 0/10 (0) | — | 10/10 (100) |
| $10^7$ | 0/10 (0) | — | 10/10 (100) |

[1]Expressed as animals dying/animals tested
[2]Expressed as animals surving/animals tested WE2102 virus was demonstrated to be highly attenuated and killed only two of twenty mice when inoculated subcutaneously with the highest dosage of virus ($10^7$ PFU). All mice were challenged 3 weeks later with $10^5$ PFU of CBA/87 virus. Mice previously immunized with $10^5$ PFU or more of WE2102 survived with no noticeable symptoms. Thus, an effective immunizing dose of WE2102 is at least 100 fold less than that required to kill C57BL6 mice. These results further indicate that the Glu to Lys change at position 182 of the E2 glycoprotein is responsible for restoring viability to viruses containing a deletion of the furin cleavage site in the WEE glycoproteins and that WE2102 virus is an effective attenuated vaccine virus.

TABLE 7

Subcutaneous Inoculation of C57BL/6 Mice with recombinant WEE virus strain 2102 confers protection against a lethal challenge

| Virus Strain Dose | Mortality[1] (%) | Mean Day to Death | Challenge[2] (%) |
|---|---|---|---|
| WE2100 | | | |
| $10^3$ | 0/10 (0) | 16 | 3/10 (30) |
| $10^5$ | 1/10 (10) | | 9/9 (100) |
| $10^7$ | 0/10 (0) | | 10/10 (100) |
| WE2102 | | | |
| $10^3$ | 0/20 (0) | — | 9/20 (45) |
| $10^5$ | 0/20 (0) | — | 18/20 (90) |
| $10^7$ | 2/20 (0) | 14 | 18/18 (100) |

TABLE 7-continued

Subcutaneous Inoculation of C57BL/6 Mice with recombinant WEE virus strain 2102 confers protection against a lethal challenge

| Virus Strain Dose | Mortality[1] (%) | Mean Day to Death | Challenge[2] (%) |
|---|---|---|---|
| WE2000 | | | |
| $10^5$ | 10/10 (100) | 9.2 | |

[1]Expressed as animals dying/animals tested
[2]Expressed as animals surving/animals tested

Attenuated VEE IE

EXAMPLE 4

Sequence Analysis. Genomic RNA from VEE IE Strain 68U201 was isolated and reverse transcription of the genomic RNA followed by polymerase chain reaction (RT-PCR) was used to generate cDNA of the virus. Initial sequencing of the strain 68U201 genome employed oligonucleotide primers based on existing VEE IE sequence and VEE IA/B sequence. After a partial sequence of strain 68U201 was determined, oligonucleotides specific to the strain 68U201 sequence were used to obtain a complete sequence of the strain 68U201 viral genome. The exact 5' end of the genome was determined by PCR/RACE technique (Frohman et al. [1988] *Proc. Natl. Acad. Sci. U.S.A.* 85:8998–9002). The entire strain 68U201 viral genomes consists of 11,464 nucleotides, excluding the poly-A sequence (Oberste et al. [1996] *Virology* 219: 314–320).

EXAMPLE 5

Construction of Full-length, Live Clones

Figure 4:
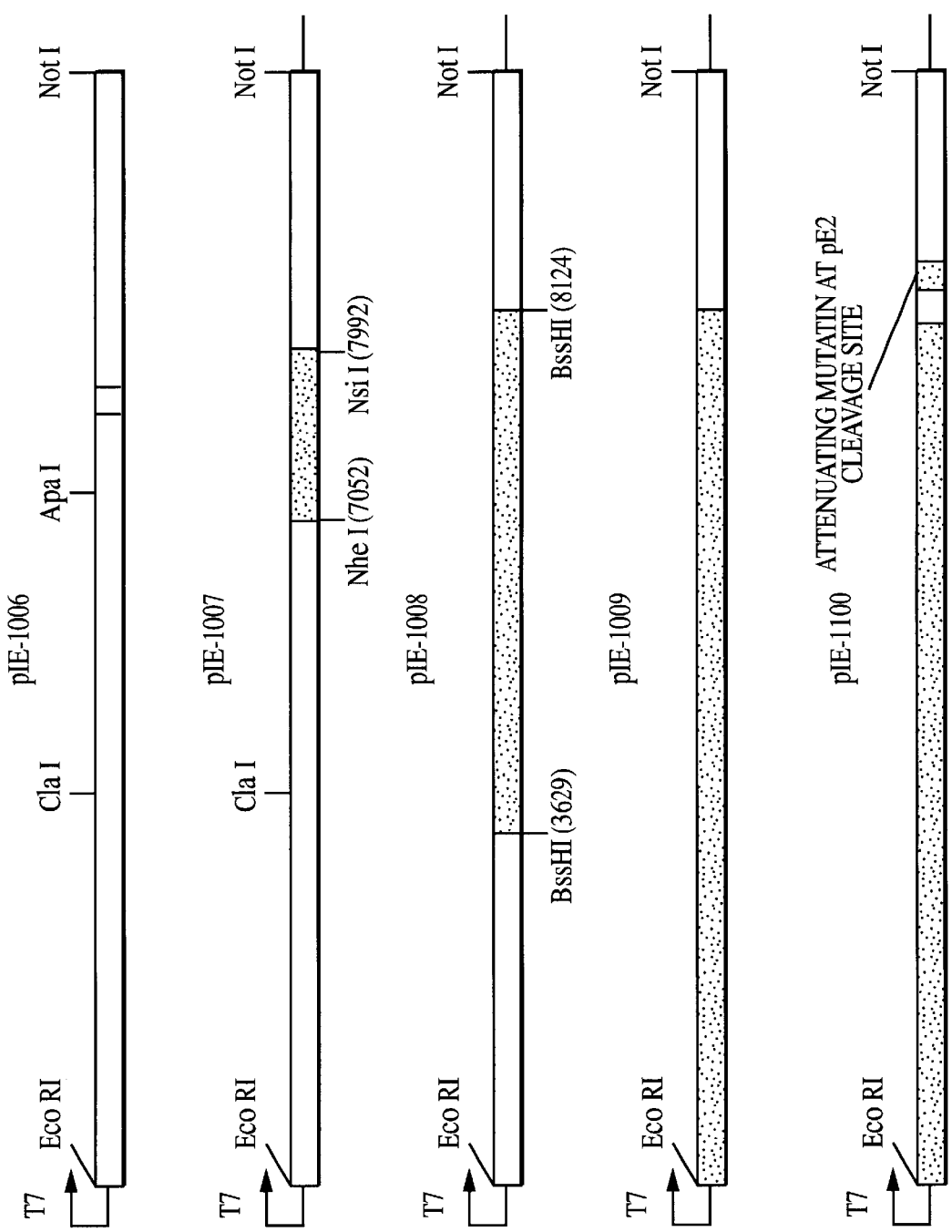
FIG. 4. Derivation of virulent VEE IE clone. Constructions of cDNA encoding the entire genome of cloned strain 68 U201 are shown. The relevent cloning sites and genetic markers are indicated above each clone. The first full-length clone produced that replicated in vitro after transfection of the RNA transcribed from the T7 promoter, was pIE-1006. Further modifications to this clone were carried out in order to obtain pIE-1009 that had the in vitro and in vivo characteristics of the parental, biological isolate, strain 68U201. With a fully virulent clone, pIE-1009 available, specific attenuating mutations were introduced into pIE-1009 to generate the attenuated clone, pIE1100. Drawings are not to scale. Shaded areas represent regions of pIE1006 that were replaced or mutated to generate new clones.
Figure 5:
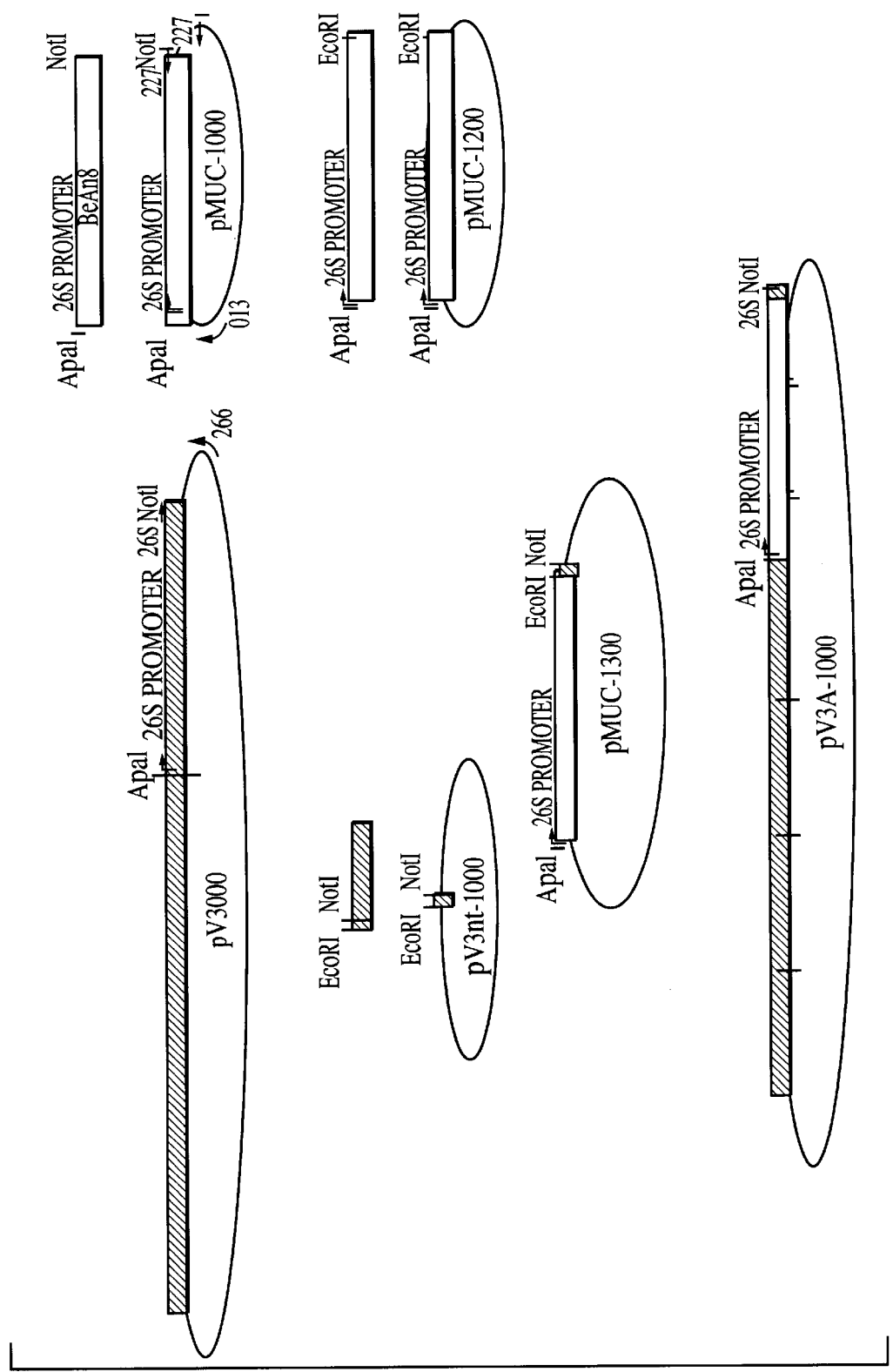
FIG. 5. Construction of IAB-IIIA cDNA chimeric clone pV3A-1000.

Using oligonucleotides specific to the VEE IE strain 68U201 sequence, RT-PCR of strain 68U201 viral RNA was carried out to generate numerous cDNA fragments that were subsequently cloned. These clones were used to assemble a full-length cDNA of strain 68U201 in a plasmid situated such that the cDNA could be precisely transcribed in an in vitro transcription reaction employing T7 polymerase. The first nucleotide downstream of the T7 promoter is a G followed by a cDNA encoding the entire strain 68U201 genome, including poly-A sequence. For the purposes of run off in vitro transcription, a unique endonuclease restriction site (NotI) follows the poly-A sequence (FIG. 4). DNA sequences encoding the T7 promoter and the strain 68U201 genome were cloned into a suitable plasmid for propagation and selection in *E. coli*. Oligonucleotides relevant to construction of full-length infectious clones are shown in Table 8.

TABLE 8

| | | |
|---|---|---|
| 0077 | CTAAGAGGGGCCCCTATATC | (SEQ ID NQ: 16) |
| 0111 | GCGGAATTCTAATACGACTCACTATAGATGGGCGGCGCATGAGAG | (SEQ ID NO:17) |
| 0113 | TGACCGCGGGACCTCTGTCCAC (SEQ ID NO: 18) | |
| 0126 | AAGTGCATCGATTCAGCG (SEQ ID NO:19) | |
| 0136 | CTGAAATGTCCAGGATCCACGGAGGAGCTG (SEQ ID NO: 20) | |
| 0137 | CAGCTCCTCCGTGGATCCTGGACATTTCAG (SEQ ID NO: 21) | |
| 0140 | GACTGCGGCCGCTTTTTTTTTTTGAAATATTAAAAACAAAATCC | (SEQ ID NO: 22) |
| 0220 | CGAGAATCGATGCACTTCAGCC (SEQ ID NO: 23) | |

Descriptions of oligonucleotides are as follows: 0077 introduces an ApaI endonuclease restriction site along with a serine to proline mutation within the coding region of nsP4. 0111 encodes an EcoRI endonuclease restriction site followed by the T7 promoter, a single G, and the first 18 nucleotides of the VEE IE genome. 0126 introduces a ClaI endonuclease restriction site within the coding region of nsP3 and was used in combination with 0220. 0113 was used to remove an ApaI endonuclease restriction site within the structural genes. 0140 encodes a unique NotI endonuclease restriction site followed by a 12 T's, and the reverse complement of the last 21 nucleotides of the VEE IE. A NotI site at the end of the cDNA encoding the VEE IE genome allowed for run-off transcription after digestion of the plasmid with NotI. 0220 introduces a ClaI endonuclease restriction site within the coding region of nsP3 and was used in combination with 0126. Minor alterations of the nucleotide sequence using 0077, 0113, 0126, and 0220 facilitated assembly of the full-length clones and allowed for rapid diagnostic analysis of virus generated from these clones by RT/PCR methods.

The full-length clone obtained, pIE1006, was transcribed in vitro using T7 polymerase of NotI-linearized plasmid and the RNA transfected into BHK-21 cells (FIG. 4). The phenotype of the resulting virus was markedly different from the parent virus (strain 68U201) from which the cDNA was derived. The virus derived from pIE1006 in vitro transcribed RNA, VIE1006, gave rise to small plaques upon infection of target monolayers (Table 9). In attempts to recover the phenotypic characteristics of strain 68U201, regions of the pIE1006 clone were replaced with cDNA generated by RT-PCR from strain 68U201 RNA. Three subsequent full-length, live clones were constructed by replacing pIE1006 sequences with 928, 4492, and 8130 nucleotides generated by RT-PCR of strain 68U201 RNA. These clones were designated pIE1007, pIE1008 and pIE1009; and viruses derived from these clones were designated VIE1007, VIE1008 and VIE1009, respectively. These clones are shown in FIG. 4. The relevant cloning sites and genetic markers are indicated above each clone. Numbers indicate the corresponding nucleotides in the strain 68U201 genome. The T7 promoter is shown. Drawings are not to scale. Shaded areas represent regions of pIE1006 that were replaced or mutated to generate new clones. The characteristics of these viruses are described below.

EXAMPLE 6

Assessment of Viruses Derived from Various Clones.

The viruses VIE1006, VIE1007, VIE1008 and VIE1009 were derived from plasmids pIE1006, pIE1007, pIE1008, and pIE1009, respectively. Analysis of virus derived from these clones by plaque assay is shown in Table 9. Plaque size was determined by infection of Vero cell monolayers followed by agarose overlay.

Analysis of virus derived from these clones (Table 9) by plaque assay indicated that VIE1007 gave the same plaque morphology as VIE1006 and therefore was not studied further. The VIE1008 produced larger plaques in comparison to VIE1006, and the VIE1009 virus gave rise to the largest sized plaques of the four viruses tested. Plaques generated by VIE1009 were similar to those produced by the parental virus, strain 68U201.

TABLE 9

In vitro analysis of virus derived from molecular clones of VEE IE strain 68U201

| Virus Strain[1] | Plaque Size |
|---|---|
| VIE1006 | small |
| VIE1007 | small |
| VIE1008 | medium |
| VIE1009 | large |
| VEE IE 68U201 | large |

EXAMPLE 7

In Vivo studies of VEE IE Vaccine Candidates.

The distinct plaque morphologies of VIE1006, VIE1008, and VIE1009 suggested that these viruses may behave differently in vivo. To assess the relative virulence of the cloned derivatives of strain 68U201, mice were initially inoculated with subcutaneously VIE1006, VIE1008, and VIE1009 viruses (Table 10). Mice infected with VIE1006 and VIE1008 were not adversely affected by these viruses as assayed by the number of mice surviving the infection. VIE1009 proved to be as virulent as strain 68U201, causing death in all of the animals infected (Table 10). Immunogenicity of the different viruses inferred by the demonstration of a protective immune response and was determined by back challenge of surviving animals in the virulence assay with approximately $10^4$ pfu of the virulent, parental virus, strain 68U201. Back challenge was performed four weeks after the initial inoculation.

TABLE 10

In vivo analysis of virus derived from molecular clones of VEE IE strain 68U201

| Virus Strain[1] | Mortality[2] | Challenge[3] |
|---|---|---|
| VIE1006 | 0/10 | 10/10 |
| V1E1008 | 0/10 | 10/10 |
| VIE1009 | 10/10 | nd |
| VEE IE 68U201 | nd | 1/10 |

[1]Initial inoculation with approximately $10^4$ PFU of each virus with the exception of VEE IE 68U201 which were left untreated until challenge phase of experiment.
[2]Expressed as animals dying/animals tested.
[3]Expressed as animals surviving/animals tested. All animals were challenged with approximately $10^4$ PFU of VEE IE strain 68U201 four weeks after the initial inoculation.

EXAMPLE 8

Construction of a Full-length, Molecularly Attenuated VEE IE Clone.

With the availability of a full-length virulent clone, specific attenuating mutations were introduced into the structural genes of the virus by site-directed mutagenesis. A deletion mutation was used instead of a point mutation because of the inability of viral RNA replication to repair such mutations. The glycoproteins of VEE IE are produced as a poly-protein precursor, PE2. The junction between the E3 and E2 proteins is cleaved by a furin-like cellular protease. The amino acid sequence of the presumed furin-like protease cleavage site of strain 68U201 is RGKR. The nucleotides encoding these four amino acids of the furin-like cleavage site between the E3 and E2 proteins were deleted from the pIE1009 clone and the resulting "cleavage deletion" clone was designated pIE1100. The oligonucleotides used to generate the cleavage deletion mutation are shown in Table 8. Oligonucleotide 0136 encodes a cleavage deletion mutation that eliminates the four amino acid furin-like cleavage site found in PE2 and was used in combination with oligonucleotide 0137. 0137 encodes the reverse complement of 0136.

Transfection of RNA transcribed from pIE1100 into tissue culture cells required extended incubation periods before viral cytopathic effect became apparent in the cultured cells. This extended incubation period is indicative of transcripts from full-length clones possessing mutations that partially inhibit viral replication. However, such mutations can be suppressed by second-site mutations which arise randomnly via the error prone process of alphavirus replication, resulting in variants with enhanced replication ability. In fact, the culture media from cells transfected with RNA transcribed from pIE1100 contained low titers of infectious virus, VIE1100, which could be amplified to high titer ($4 \times 10^7$ PFU/ml) upon subsequent passage. Biochemical analysis showed that this virus had an uncleaved PE2 protein indicating that the cleavage deletion mutation totally prevented proteolytic processing of the surface E2 glycoprotein precursor. The efficacy of VIE1100 virus to serve as a vaccine was evaluated in mice as described below.

One specific suppressor mutation is thought to reside at nucleotide 10,181 of the VEE IE genome, a C to U nucleotide substitution resulting in an amino acid change from Serine to Leucine in the E1 protein positon #57. Ability of this mutation to suppress the lethal nature of the furin cleavage site deletion mutation was assessed. The cDNA of pIE1100 was mutated by changing nucleotide 10,181 from a C to T. This introduced a serine to leucine change at amino acid number 57 of E1, a mutation found within the stock of VIE1100. The resulting clone was designated pVIE1150. Transfection of RNA from pVIE1150 into BHK21 cells lead to the production of approximately $10^6$ PFU/ml of virus in the supernatant of the transfected cells at 48 hours post-transfection.

EXAMPLE 9
Vaccine Studies with a Full-length, Molecularly Attenuated Virus.

Balb/C mice were inoculated with VIE1100 virus at various doses ($10^4$, $10^6$, and $10^7$ PFU per mouse), and was found to be completely attenuated at a dose 100,000 times higher than that required to cause lethal disease by the parent virus, strain 68U201 (Table 10). Subsequent challenge of these animals with virulent strain 68U201 demonstrated that immunization with VIE1100 virus provided complete protection from lethal virus challenge (Table 11).

TABLE 11

Vaccination study with VIE1100

| Virus Strain Dose | Mortality[1] | Challenge[2] |
|---|---|---|
| VIE1100 | | |
| $10^4$ | 10/10 | 10/10 |
| $10^6$ | 10/10 | 10/10 |
| $10^7$ | 10/10 | 10/10 |
| Mock Vaccinated | 0/10 | 0/10 |

[1]Expressed as animals dying/animals tested.
[2]Expressed as animals surviving/animals tested after inoculation with $10^4$PFU of VEE IE strain 68U201

EXAMPLE 10
Properties of a WEE-EEE chimeric virus.

Figure 3:
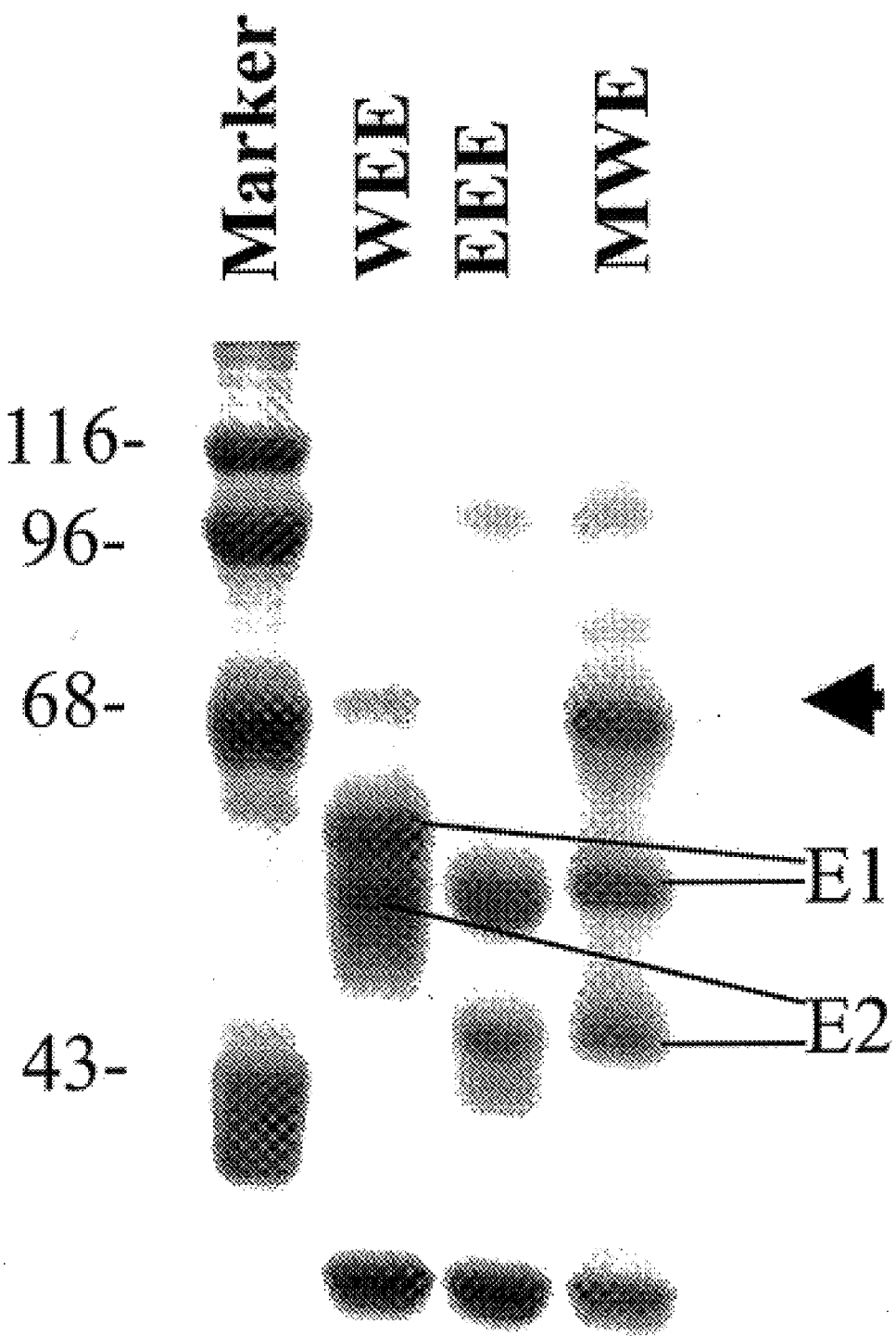
FIG. 3. Polypeptide profiles of western equine encephalitis virus (WEE), eastern equine encephalitis (EEE) and chimeric virus, MWE. Samples of purified virus were analyzed by electrophoresis on 10% polyacrylamide gels and stained with Comassie Brilliant blue. Molecular weight markers (MW) are shown and molecular weights are indicated in daltons X $10^{-3}$. Position of contaminating bovine serum albumin is indicated by arrow.

Based upon similarities of amino acid sequences of the carboxy terminal portion of NSP-4 and the amino terminal portion of the capsid proteins of WEE, EEE and Sindbis virus, it has been suggested that WEE virus arose by recombination between EEE and a Sindbis virus ancestor (Hahn et al. [1988] Proc. Natl. Acad. Sci. U.S.A. 85: 5997–6001). The capsid genes of both WEE and EEE contain a highly conserved sequence with a unique Bln I site 76 nucleotides downstream of the initiation codon. We utilized this site to insert the structural protein sequences of EEE into pWE5-18 in order to construct a full length clone encoding a chimeric virus. Plasmid pMWE-7 is a full length clone consisting of the 5' non-coding sequence, nonstructural genes, 26S promoter and the first 25 codons for the capsid protein of WEE CBA/87 fused to the structural protein genes and 3' non-coding sequence of EEE strain Fla91-4679. Transfection of BHK cells with RNA transcribed from pMWE-7 resulted in complete destruction of the monolayer and release of high yields of virus. SDS-polyacrylamide gel electrophoresis of the purified virus demonstrated that the virus is composed of polypeptides which comigrate with those of EEE and not of WEE, indicating that the virus is a chimera (FIG. 3).

Injection of mice with the MWE chimeric virus killed mice only sporadically, suggesting that fusion of the sequences of the two viruses resulted in significant attenuation compared to the parent WE2000 virus (Table 12). Mice immunized with MWE-7 developed significant neutralizing antibody titers and resisted a lethal EEE Fla91-1467 challenge when immunized with greater than $10^5$ plaque forming units of MWE-7 virus. The neutralizing antibody response after challenge was not significantly elevated indicating that the immunization with the chimeric virus effectively prevented infection by a lethal EEE challenge. Therefore, a chimeric virus derived by combining the structural protein genes of EEE with the non-structural proteins genes of WEE may serve as a safe, effective approach to development of a vaccine for EEE virus.

TABLE 12

Immunization of C57BL6 Mice with an WEE/EEE Chimeric Virus Confers Protection Against a Lethal EEE Challenge

| Virus Strain Dose | Mortality[1] | Mean Day to Death | Challenge[2] |
|---|---|---|---|
| WE2000 | | | |
| $10^5$ | 10/10 (100) | 8.5 | |
| MWE7 | | | |
| $10^3$ | 0/10 (0) | | 6/10 (60) |
| $10^5$ | 1/10 (10) | 8.0 | 9/9 (100) |
| $10^7$ | 0/10 (0)[3] | | 9/9 (100) |
| Saline Control | 0/10 (0) | | 0/10 (0) |

[1]Expressed as animals dying/animals tested
[2]Expressed as animals surving/animals tested
[3]One animal died during pre-challenge bleed

EXAMPLE 12

VEE IIIA Chimera
Construction of IAB-IIIA cDNA Chimeric Clone (pV3A-1000)

BeAn8 (wild type Mucambo or VEE IIIA) cDNA was amplified with primers 128 and 140 (Table 13) to generate a PCR fragment of the entire 26S region of BeAn8. Primer 128 incorporated an ApaI site just upstream of the BeAn8 26S promoter to facilitate cloning into pV3000. Primer 140 introduced a NotI site just downstream of the poly(A) tract which would also facilitate cloning into pV3000 as well as enable run-off transcription. This 128/140 PCR fragment was cloned into pBluescript SK+ vector using the ApaI and NotI sites and was termed pMUC-1000.

To replace the BeAn8 3' nontranslated region (3' NTR) in pMUC-1000 with the corresponding region in pV3000, an EcoRI site was introduced immediately downstream of the E1 stop codon in both pMUC-1000 and pV3000 using the primer pairs 013/227 and 225/226, respectively. The 013 primer is a universal primer found in the pBluescript SK+ vector and the 227 primer was designed to introduce an EcoRI site in pMUC-1000. The 225 primer introduced an EcoRI site in pV3000 and the 226 primer is located in the vector, TotoX. The 013/227 and 225/226 PCR fragments were separately cloned into the pBluescript SK+ vector producing PMUC-1200 and pV3nt-1000, respectively. The 3' NTR encoded in pV3nt-1000 was shuttled into pMUC-1200 using the EcoRI site and the NotI site to produce pMUC1300.

The full-length chimeric cDNA clone, pV3A-1000, was constructed by shuttling the structural genes encoded in pMUC-1300 into the pV3000 nonstructural domain using the ApaI site and NotI site.

TABLE 13

Primers for construction of the PV3A-1000

| | | (SEQ ID NO: 24) |
|---|---|---|
| 013 | AACAGCTATGACCATG | |
| | | (SEQ ID NO: 25) |

TABLE 13-continued

Primers for construction of the PV3A-1000

| 128 | CTGAGAGGGGCCCCAGTAAC |
|---|---|
| | (SEQ ID NO: 26) |
| 140 | GACTGCGGCCGCTTTTTTTTTTTGAAATATTAAAAA |
| | (SEQ ID NO: 27) |
| 225 | CCAGAAACATAATTGAATTCAGCAGCAATTG |
| | (SEQ ID NO: 28) |
| 226 | CTTTATCCGCCTCCATCC |
| | (SEQ ID NO: 29) |
| 227 | CCAATCGCTGCTGAATTCTAATTATGTTTCTG |

Five week old C57BL6 mice were used in a challenge study (Table 14). All mice immunized with $10^7$ PFU of pV3A-1000 produced neutralizing antibodies. Mice were challenged with $10^7$ PFU of 900807 (a Mucambo virus from Trinidad). The geometric mean neutralizing antibody titer in mice inoculated with $10^7$, $10^5$, and $10^3$ PFU of pV3A-1000 was 9800, 8800, and 7000 respectively.

TABLE 14

Results from challenge studies

| | Fraction of mice sick/inoc | Fraction of mice dead/inoc | Average days to onset of illness | Average days to death |
|---|---|---|---|---|
| Immunized with pV3A-1000 | 0/20 | 0/20 | N/A | N/A |
| Unvaccinated | 19/20 | 12/20 | 6.2 | 10.5 |

What is claimed is:

1. A DNA comprising an isolated and purified western equine encephalitis (WEE) virus cDNA fragament coding for infectious western equine encephalitis virus genome, said cDNA fragment containing a deletion in the E3-E2 cleavage site and a supressor mutation.

2. The DNA according to claim 1 wherein said suppressor mutation is a substitution of glutamic acid at codon 182 of E2 to lysine.

3. The DNA according to claim 1 wherein said suppressor mutation is a substitution of glutamic acid at codon 181 of E2 to lysine.

4. A DNA according to claim 1 wherein said WEE cDNA fragment is operably linked to a promoter such that said cDNA is transcribed.

5. An attenuated WEE virus RNA transcript encoded by the cDNA fragment of claim 1.

6. A DNA according to claim 2 wherein said WEE cDNA fragment is operably linked to a promoter such that said cDNA is transcribed.

7. An attenuated WEE virus RNA transcript encoded by the cDNA fragment of claim 2.

8. A DNA according to claim 3 wherein said WEE cDNA fragment is operably linked to a promoter such that said cDNA is transcribed.

9. An attenuated WEE virus RNA transcript encoded by the cDNA fragment of claim 3.

10. Attenuated WEE virus particles containing an RNA transcript according to claim 5.

11. Attenuated WEE virus particles containing an RNA transcript according to claim 7.

12. Attenuated WEE virus particles containing an RNA transcript according to claim 9.

13. A live attenuated western equine encephalitis (WEE) virus vaccine comprising attenuated western equine encephalitis virus according to claim 10.

14. A live attenuated western equine encephalitis (WEE) virus vaccine comprising attenuated Western Equine Encephalitis virus according to claim 11.

15. A live attenuated western equine encephalitis (WEE) virus vaccine comprising attenuated western equine encephalitis virus according to claim 12.

16. A pharmaceutical formulation comprising attenuated WEE virus particles according to claim 10 in an effective immunogenic amount in a pharmaceutically acceptable carrier.

17. A pharmaceutical formulation comprising attenuated WEE virus particles according to claim 11 in an effective immunogenic amount in a pharmaceutically acceptable carrier.

18. A pharmaceutical formulation comprising attenuated WEE virus particles according to claim 12 in an effective immunogenic amount in a pharmaceutically acceptable carrier.

19. An inactivated western equine encephalitis virus (WEE) vaccine comprising attenuated WEE according to claim 10 wherein said attenuated WEE is inactivated.

20. An inactivated western equine encephalitis virus (WEE) vaccine comprising attenuated WEE according to claim 11 wherein said attenuated WEE is inactivated.

21. An inactivated western equine encephalitis virus (WEE) vaccine comprising attenuated WEE according to claim 12 wherein said attenuated WEE is further inactivated.

22. An attenuated western equine encephalitis virus wherein said virus comprises an attenuating mutation selected from the group consisting of: a C to T change at nucleotide 7 of the 5' noncoding region of the WEE genome, a A to G change at nucleotide 13 of the 5' noncoding region of the WEE genome, a T to A change at nucleotide 25 of the 5' noncoding region of the WEE genome, and a deletion of an A at nucleotide 22 of the 5' noncoding region of the WEE genome.

* * * * *

SEQUENCE LISTING (1) GENERAL INFORMATION:

(iii) NUMBER OF SEQUENCES:29

(2) INFORMATION FOR SEQ ID NO:1:

(i) SEQUENCE CHARACTERISTICS:
(A) LENGTH: 11492 base pairs
(B) TYPE: Nucleic acid
(C) STRANDEDNESS:Double
(D) TOPOLOGY: Linear (ix) FEATURE: OTHER INFORMATION: N at all occurences is = unknown.

(ix) FEATURE: OTHER INFORMATION: K at all occurences is = G or T (ii) SEQUENCE DESCRIPTION: SEQ ID NO:1:

```
ATAGGGCATG GTATAGAGGC ACCTACCCTA CAAACAAATC      40
GATCCAATAT GGAAAGAATT CACGTTGACT TAGACGCTGA      80
CAGCCCATAT GTCAAGTCGT TACAGCGGAC GTTTCCACAA     120
TTTGAGATCG AAGCAAGGCA GGTCACTGAC AATGACCATG     160
CCAATGCCAG AGCGTTTTCG CATGTGGCAA CAAAGCTCAT     200
TGAGAGCGAA GTCGACCGGG ACCAAGTTAT CTTGGACATT     240
GGAAGTGCGC CCGTCAGACA TGCACATTCC AACCACCGCT     280
ATCATTGTAT CTGCCCCATG ATAAGCGCTG AAGACCCGGA     320
CAGACTACAG CGGTATGCAG AAAGACTTAA GAGAAGTGAC     360
ATGTACCGAC AAGAATATAG CCTCTNAAGG CGGCAGACCT     400
GCTGGAAGTC ATGTCCACAC CAGACGCAGA GACTCCATCT     440
CTGTGTATGC ACACAGACGC CACGTGTAGG TACTTTGGAA     480
GTGTANGCAG TATACCAAGA TGTGTACGCA GTCCATGCAC     520
CGACATCAAT CTACCACCAG GCGCTTAAAG GAGTTAGGAC     560
AATTTACTGG ATAGGTTTTG ACACGACCCC TTTTATGTAC     600
AAAAACATGG CAGGTTCCTA CCCTACTTAC AACACAAACT     640
```

| | |
|---|---|
| GGGCCGACGA GAGAGTATTG GAAGCACGTA ACATTGGCCT | 680 |
| CGGTAACTCA GATCTTCAGG AGAGCAGACT TGGAAAACTT | 720 |
| TCAATCCTTA GGAAGAAGAG GCTCCAACCT ACTGATAAGA | 760 |
| TCATATTCTC GGTTGGTTCA ACAATCTACA CAGAGGATAG | 800 |
| ATCACTGTTA CGTAGCTGGC ATCTTCCAAA CGTGTTCCAC | 840 |
| CTGAAAGGAA AGTCTNACTT CACAGGTAGA TGTGGGACCA | 880 |
| TTGTCAGCTG TGAAGGGTAT GTCATCAAAA AGATAACGAT | 920 |
| CAGCCCAGGA CTATACGGTA AAGTTGAGAA CTTGGCGTCC | 960 |
| ACGATGCATC GCGAGGGTTT CTTGAGTTGC AAAGTCACAG | 1000 |
| ATACGCTGCG CGGCGAGAGG GTTTCTTTTG CTGTGTGTAC | 1040 |
| GTATGTACCA GCCACACTTT GCGATCAGAT GACAGGGAGG | 1080 |
| GCTCAACCAA CGGATTGTCG TCAATGGTAG GACGCAAAGA | 1120 |
| AATACTNACA CAATGCAGAA CTATCTATTA CCAGTGGTCG | 1160 |
| CCCAGGCGTT TTCCAGGTGG GCGCGTGNAC ATCGTGCCGA | 1200 |
| CTTGGACGAC GAGAAGGAGC TAGGGGTGCG GGAGCGCACT | 1240 |
| CTTACTATGG GCTGCTGCTG GGCTTTCAAG ACCCAGAAAA | 1280 |
| TTACATCCAT CTACAAGAAG CCTGGTACGC AAACAAATTA | 1320 |
| AGAAAGTACC TGCCGTCTTT TGACTCATTT GTGATTCCGA | 1360 |
| CGCCTTACCA GCCACGCGGG GGCTCGAATA TGGGCCTTCC | 1400 |
| GCCGTNAGGC TCAAGCTGCT GCTTGAACCA ACTGTCAAAC | 1440 |
| CCGCACCGGC TATTACAATG GCCGATGTGG AGCACCTGCG | 1480 |
| TGGCTTACAG CAAGAAGCTG AAGAAGTGGC TGCAGCGGGA | 1520 |
| AGAGATCAGA GAAGCCCTGC CACCCTTGCT CCCTGAAATA | 1560 |
| GAAAAAGAGA CCGTAGAGGC AGAAGTAGAC CTCATTATGC | 1600 |
| AAGAGGCAGG AGCAGGTAGC GTGGAGACAC CNACGAGGAC | 1640 |
| ATATCAAGGT AACAAGTTAC CCAGGTGNAA GAGAAGATTG | 1680 |
| GGTCTTATCC CTATACTTTC ACCCCAGGCG GTTTTANAAT | 1720 |
| NGTNAAAAAC TGGCGTGTAT CCACCCATTG GCGGAACAAG | 1760 |
| TACTGGTAAT GACTCACAAA GGCAGGGCCG GGCGATACAA | 1800 |
| AGTCGAGCCA TACCACGGTA NGGTCATTGT ACCCAGAAGG | 1840 |
| GACGGCGGGT CCCTGTTCAA GACTTTCAGG CACTGAGTGA | 1880 |
| GAGCGCCACG ATCGTTTTCA ACGAGAGGGA GTTCGTAAAC | 1920 |
| CAGATATTTT GCACCCACAT CGCAAGCKTT TCAACTATAG | 1960 |
| TGAGTCGCTA TTCACTGAC GAAGAGTACT ATAAGATTGT | 2000 |
| AAAGACTCAG GACGCAGACT CAGAATACGT CTTTGACATT | 2040 |
| GACGCACGAA AGTGTGTTAA GCGAGAAGAC GCAGGTCCCT | 2080 |
| TGTGCCTAAC TGGTGATCTG GTAGATCCAC CATTTCACGA | 2120 |
| GTTTGCGTAC GAGAGTCTCA AGACACGACC AGCAGCACCT | 2160 |
| CACAAAGTCC CAACCATCGG AGTCTATGGA GTGCCAGGTT | 2200 |
| CAGGTAAATC TGGGATCATC AAAAGCGCTG TGACTAAGAA | 2240 |

```
AGATCTGGTT GTGAGTGCGA AGAAGGAAAA CTGCGCAGAA            2280

ATTATCAGGG ATGTAAGGAG GATGAGACGT ATGGATGTTG            2320

CTGCTAGGAC TGTTGATTCA GTGCTTCTAA ATGGGGTTAA            2360

GCACCCCGTT AACACCCTGT ACATTGATGA GGCATTTGCC            2400

TGCCATGCAG GGACGCTGCT GGCACTGATT GCCATCGTCA            2440

AACCTAAGAA AGTGGTATTG TGCGGGGACC CAAAACAATG            2480

CGGCTTCTTT AACATGATGT GCCTGAAAGT ACATTTTAAC            2520

CATGACATAT GCACTGAGGT GTACCACAAA AGCATCTCTA            2560

GGAGGTGCAC ACAGACTGTA ACCGCCATTG TCTCCACGCT            2600

CTTCTACGAC AAGCGAATGA AGACGGTTAA CCCATGTGCT            2640

GACAAAATCA TCATAGATAC CACAGGGACC ACAAAGCCGC            2680

ACAAAGATGA TCTGATTCTA ACCTGTTTCA GAGGATGGGT            2720

GAAACAGCTA CAGATTGACT ATAAAAATCA TGAAATCATG            2760

ACTGCGGCTG CATCGCAAGG ACTTACGCGG AAAGGCGTTT            2800

ATGCTGTCAG GTACAAAGTC AACGAGAATC CACTCTACTC            2840

GCAGACTTCT GAGCACGTGA ACGTGTTAGT TACACGCACA            2880

GAAAAACGCA TTGTCTGGAA GACGCTAGCT GGTGACCCCT            2920

GGATAAAGAC ACTTACAGCT AAATACTCCG GGGATTTCAC            2960

GGCTTCATTG GACGACTGGC AACGCGAACA CGACGCTATT            3000

ATGGCACGCG TTCTTGATAA GCCGCAGACA GCTGATGTGT            3040

TCCAGAATAA GGTGAACGTC TGCTGGGCGA AGGCTTTAGA            3080

GCCAGTCTTG GCCACGGCCA ACATTGTGCT GACGAGACAG            3120

CAGTGGGAGA CGTTGCACCC ATTCAAGCAT GACAGAGCGT            3160

ACTCACCTGA AATGGCACTG AACTTCTTTT GCACCAGGTT            3200

CTTTGGTGTA GACCTGGACA GTGGGTTGTT TTCCGCTCCT            3240

ACCGTCGCAC TTACTTACAG GGATCAGCAC TGGGACAACT            3280

CGCCAGGGAA GAACATGTAT GGGCTTAATA GAGAGGTAGC            3320

AAAGGAGCTG TCACGGCGAT ATCCGTGCAT CACAAAAGCG            3360

GTTGACACAG GCAGGGTAGC TGATATAAGG AATAATACCA            3400

TCAAGGACTA CTCTCCAACA ATTAATGTGG TTCCATTAAA            3440

TCGCCGGTTG CCCCACTCGC TGATCGTTGA CCACAAAGGA            3480

CAGGGTACAA CTGATCACAG TGGATTCCTA TCTAAGATGA            3520

ATGGCAAATC TGTGTTGGTG ATCGGCGATC CTATCAGCAT            3560

TCCTGGGAAG AAAGTAGAGT CCATGGGTCC ATTGCCCACT            3600

AATACCATCA GGTGTGATCT CGATTTGGGA ATACCTAGCC            3640

ATGTCGGTAA ATATGACATT ATATTTGTCA ATGTTAGGAC            3680

CCCATACAAG AACCATCACT ACCAACAGTG CGAGGATCAC            3720

GCTATCCACC ACAGCATGCT AACGTGTAAG GCTGTCCACC            3760

ACCTGAACAC TGGCGGAACA TGTGTGGCCA TAGGGTATGG            3800
```

-continued

| | |
|---|---|
| ACTTGCTGAT CGCGCAACCG AGAATATCAT CACTGCGGTG | 3840 |
| GCTCGCTCAT TTAGGTTTAC CCGTGTCTGT CAGCCTAAGA | 3880 |
| ACACTGCCGA AAATACTGAG GTTCTCTTCG TGTTCTTCGG | 3920 |
| CAAGGACAAC GGCAACCACA CACATGACCA GGACAGACTC | 3960 |
| GGTGTAGTGC TTGACAACAT CTACCAAGGG TCAACCAGGT | 4000 |
| ACGAGGCAGG GAGAGCTCCA GCGTACAGAG TGATCAGAGG | 4040 |
| TGACATTAGC AAGAGCGCTG ACCAAGCTAT CGTTAATGCT | 4080 |
| GCTAATAGCA AAGGTCAACC AGGTTCCGGA GTGTGCGGTG | 4120 |
| CACTGTACCG AAAATGGCCG GCTGCTTTTG ATAGACAGCC | 4160 |
| AATAGCTGTC GGGACGGCTA GACTTGTGAA GCACGAACCG | 4200 |
| CTCATCATAC ATGCTGTAGG ACCGAATTTT TCTAAGATGC | 4240 |
| CGGAACGAGA GGGCGACCTT AAGCTCGCAG CTGCCTACAT | 4280 |
| GAGCATAGCG TCCATCGTCA ACGCTGAGCG GATTACTAAA | 4320 |
| ATATCAGTAC CGCTACTGTC AACTGGCATC TATTCTGGTG | 4360 |
| GCAAAGATCG AGTGATGCAA TCATTGCATC ACTTGTTCAC | 4400 |
| TGCTTTCGAC ACTACGGATG CCGATGTCAC CATATATTGC | 4440 |
| TTGGATAAAC AATGGGAGAC CAGGATAACC GAGGCCATTC | 4480 |
| ACCGCAAAGA AAGCGTCGAA ATACTGGATG ATGATGACAA | 4520 |
| GCCAGTAGAC ATCGACTTGG TCAGGGTCCA CCCAAACAGC | 4560 |
| TCTTTGGCAG GCAGACCAGG TTACTCCGTC AATGAGGGCA | 4600 |
| AGCTGTATTC ATACCTGGAA GGTACACGAT TCCATCAGAC | 4640 |
| CGCCAAGGAC ATTGCCGAAA TCCATGCAAT GTGGCCCAAC | 4680 |
| AAATCTGAGG CTAATGAGCA GATTTGCTTG TACATCCTGG | 4720 |
| GGGAGAGTAT GTCCAGCATC CGCTCCAAAT GCCCAGTAGA | 4760 |
| GGAGTCAGAG GCGTCTGCTC CACCTCACAC ACTTCCATGC | 4800 |
| CTGTGTAATT ACGCTATGAC GGCTGAGCGC GTATACAGGT | 4840 |
| TGCGCTCTGC GAAGAAAGAA CAGTTCGCCG TATGCTCATC | 4880 |
| ATTCCCGTTG CCGAAGTACA GGATCACAGG CGTGCAGAAG | 4920 |
| CTACAGTGCA GCAAACCAGT CCTGTTCTCA GGCGTCGTAC | 4960 |
| CACCGGCTGT ACACCCCAGG AAGTACGCGG AAATAATTCT | 5000 |
| AGAAACGCCA CCATCGCCAA CAACGACAAC CGTAATATGT | 5040 |
| GAACCAACTG TGCCAGAACG TATACCCAGT CCGGTGATTT | 5080 |
| CTAGAGCAGC AAGTGCGGAA TCACTGCTAT CGTTTGGCGG | 5120 |
| CGTCTCGTTC TCTAGCTCTG CCACACGCTC GTCAACTGCC | 5160 |
| TGGAGCGACT ATGACAGGCG GTTTGTGGTT ACAGCTGACG | 5200 |
| TGCATCAAGC GGACACGTCT ACGTGGAGCA TCCCTAGCGC | 5240 |
| TCCTGACTTG GACGTCCAGC TGCCTTCTGA CGATACTGAT | 5280 |
| TCCCACTGGA GTATTCCGAG TGCATCAGGC TTTGAAGTGA | 5320 |
| GAACACCGTC TGTACAGGAC CTAACTGCAG AGTGTGCGAG | 5360 |
| GCCTCGTGGA CTGGCCGAAA TAATGCAAGA CTTCAATACG | 5400 |

| | |
|---|---|
| GCTCCTTTCC AGTTTCTTTC GGACCACAGA CCAGTACCAG | 5440 |
| CACCACGGAG ACGCCCCATC CCATCACCTA GATCGACGGT | 5480 |
| TTCCGCACCT CCAGTTCCAA AGCCACGCAG AACTAAGTAC | 5520 |
| CAACAACCAC CAGGAGTCGC TAGGGCGATC TCAGAAGCGG | 5560 |
| AGCTGGACGA GTACATCCGT CAACATTCCA ATTGACGGTA | 5600 |
| TGAAGCGGAG CGTATATTTC TCATCGAAAC AGGCCAGGTC | 5640 |
| ACCTTCAACA GAAATCAGTA CGTCAATGTA AACTACAAGA | 5680 |
| CCCTATATTG GAACGGGCCG TCCATGAGAA GTATTAGCCC | 5720 |
| CGCGCCTCGA TCTCGAAAGA GAGAAGATGT TACAGAAGAA | 5760 |
| ACTGCAATTA TGCGCCTCNT GAAGGAAATA GAAGCAGGTA | 5800 |
| TCAATCACGA AAAGTANGAA AATATGAAAG CAATTACAGC | 5840 |
| GGAGCGACTC ATTTCTGGAT TGGGCACATA TCTATCATCA | 5880 |
| GAAGTGAATC CTGTCGAGTG TTACAGAGTC AATTATCCTG | 5920 |
| TACCAATCTA CTCGTCAACG GTAGTTAATA GGTTTTCATC | 5960 |
| AGCAGAAGTG GCCGTCAAAG TTTGCAACTT AGTCATCCAA | 6000 |
| GAGAATTACC CTACAGTAGC CAGTTATTGC ATAACAGATG | 6040 |
| AATACGATGC GTATCTTGAC ATGGTGTACG GCGCTCGTGC | 6080 |
| TGTTAGATAC AGCGCCTTTG TCCGCTNACT GAGAAGCTAC | 6120 |
| CCAAAGAAGC ATAGCTACTT GCAGCCAGAG ATAAGATCAG | 6160 |
| CTGTCCCATC ACCTATACAG AATACATTAC AAAATGTATT | 6200 |
| GCTGCAGCCA CTAAAAGGAA CTGCAACGTT ACCCAAATGC | 6240 |
| GAGAACTACC TGTTTTATTC GGCGGCATTC AACGTTGAAT | 6280 |
| GTTTCAAGAA ATACGCATGC AATGATGAGT ATTGGGATAC | 6320 |
| CTTTCGCGAT AACCCTATTC GGCTAACTAC AGAGAACGTT | 6360 |
| ACGCAATACG TGACAAAGCT GAAAGGGCCG AAAGCAGCAG | 6400 |
| CATTATTCGC AAAAACTCAC AACCTAAAAC CGTTGCAGGA | 6440 |
| GATACCAATG GACGAATTTG TCATGGTCTN AAAAGAGATG | 6480 |
| TCAAAGTTAC TCCCGGCACA AAACATACAG AGGAGCGGCC | 6520 |
| TAAGGTGCAG GTTATTCAGG CTGCAGATCC TCTCTGTACC | 6560 |
| GCTTACCTTT GCGGGATCCA TCGAGAATGT CCGTAGACTG | 6600 |
| AATGCTGTGC TTCTGCCGAA TATCCATACT CTCTTCGACA | 6640 |
| TGTCAGCGGA AGATTTTGAT GCGATTATTG CTGAACATTT | 6680 |
| CCACCACGGC GACCCAGTAT TGGAAACGGA CATCGCGTCG | 6720 |
| TTTGATAAAA GCGAAGACGA CGCTATCGCC ATTTCGGCGT | 6760 |
| TGATGATCCT CGAGGACTTA GGCGTCGACC AACCGCTCTT | 6800 |
| AGATTTGATA GAGGCGGCGT TCGGCAATAT CACATCTGTG | 6840 |
| CACCTACCTA CAGGAACGAG GTTCAAATTT GGTGCCATGA | 6880 |
| TGAAATCCGG TATGTTCTTA ACGCTGTTTG TCAACACACT | 6920 |
| AGTCAATATC ATGATTGCTA GCAGAGTACT ACGTGAACGG | 6960 |

```
TTAACCACGT CAGAGTGCGC GGCCTTATCG GCGACAATAA      7000

CATAGTGCAC GGTGTCGCTC CGACAACTTG ATGGCGGAGA      7040

GATGCGCCAC TTGGCTGAAC ATGGAAGTAA AAATTATTGA      7080

TGCAGTCATT GGTATCAAAG CACCCTACTT CTGCGGGGAT      7120

TCATCCTGGT GGATCAGATA ACGACACAGC CTGTAGGTCG      7160

CAGACCCTCT AAAAGGCTT TTTAAGCTTG GAAAACCATT       7200

GCCAGTCGAT GACACCCAAG ACTGTGACCG TCGCCGGGCA      7240

CTGCATGATG AAGCAATGCG ATGGAACAGA ATTGGAATTA      7280

CGGACGAGTT GGTGAAGGCC GTAGAATCCA GATACGAGAT      7320

CATACTGGCA GGCCTGATCA TCACGTCCCT GTCCACGTTA      7360

GCCGAAAGCG TTAAGAACTT CAAGAGCATA AGAGGGAACC      7400

CAATCACCCT CTACGGCTGA CCTAAATAGG TGACGTAGTA      7440

GACACGCACC TACCCACCGC CAAAAATGTT TCCATACCCT      7480

CAGCTGAACT TTCCACCAGT TTACCCTACA AATCCGATGG      7520

CTTACCGAGA TCCAAACCCT CCTAGGCGCC GCTGGAGGCC      7560

GTTTCGGCCC CCGCTGGCTG CTCAAATCGA AGATCTTAGG      7600

AGGTCGATAG CCAACTTAAC TTTCAAACAA CGATCACCTA      7640

ATCCGCCGCC AGGTCCGCCG CCGAAGAAGA AGAAGAGTGC      7680

TCCCAAGCCA AAACCTACTC AGCCTAAAAA GAAGAAGCAG      7720

CAAGCCAACA AGACGAAACG CAAGCCTAAA CCAGGGAAAC      7760

GACAGCGTAT GTGTATGAAG TTGGAGTCGG ACAAGACATT      7800

TCCGATCATG TTGAACGGCC AAGTGAATGG ATACGCTTGC      7840

GTTGTCGGAG GAAGGCTGAT GAAACCACTC CACGTTGAAG      7880

GAAAAATCGA TAATGAGCAA TTAGCGGCCG TGAAATTGAA      7920

GAAGGCTAGC ATGTACGACC TGGAGTATGG CGACGTTCCC      7960

CAGAATATGA AATCAGACAC GCTGCAGTAC ACCAGCGACA      8000

AACCACCGGG CTTCTACAAC TGGCACCACG GCGCAGTCCA      8040

GTATGAGAAT GGGAGATTCA CCGTACCGCG AGGAGTGGGC      8080

GGGAAAGGCG ACAGTGGAAG ACCGATCCTG GACAACAGAG      8120

GCAGAGTTGT GGCTATTGTT CTAGGAGGTG CAAACGAGGG      8160

CACGCGTACG GCGCTTTCAG TGGTCACTTG GAACCAGAAA      8200

GGGGTGACCA TCAAGGATAC CCCCGAAGGT TCTGAACCGT      8240

GGTCACTAGT TACAGCGCTG TGCGTGCTTT CGAATGTCAC      8280

ATTCCCTTGC GACAAACCAC CCGTGTGCTA TTCACTGGCG      8320

CCAGAACGAA CACTCGACGT GCTCGAGGAG AACGTCGACA      8360

ATCCAAATTA CGACACGCTG CTGGAGAACG TCTTGAAATG      8400

TCCATCACGC CGGCCCAAAC GAAGCATTAC CGATGACTTC      8440

ACGCTGACCA GTCCCTACCT GGGGTTCTGC CCGTATTGCA      8480

GACACTCAGC GCCATGTTTT AGCCCAATAA AAATTGAGAA      8520

CGTGTGGGAC GAATCTGATG ATGGGTCGAT TAGAATCCAG      8560
```

| | |
|---|---|
| GTCTCGGCAC AATTCGGCTA CAATCAGGCA GGCACTGCAG | 8600 |
| ACGTCACCAA GTTCCGGTAC ATGTCTTACG ACCACGACCA | 8640 |
| TGACATCAAG GAAGACAGTA TGGAGAAAAT AGCTATTAGT | 8680 |
| ACATCTGGAC CATGCCGTCG TCTTGGCCAC AAAGGGTACT | 8720 |
| TCCTGTTAGC TCAATGTCCT CCAGGTGACA GTGTAACCGT | 8760 |
| CAGTATCACG AGCGGAGCAT CTGAGAATTC ATGCACCGTG | 8800 |
| GAGAAAAAGA TCAGGAGGAA GTTTGTCGGT AGAGAGGAGT | 8840 |
| ACTTGTTCCC ACCTGTCCAT GGAAAGCTGG TAAAGTGCCA | 8880 |
| CGTTTACGAT CACTTGAAGG AGACGTCTGC CGGATACATA | 8920 |
| ACCATGCACA GGCCAGGCCC ACACGCGTAT AAGTCCTATC | 8960 |
| TGGAGGAAGC GTCAGGCGAA GTGTACATTA AACCACCTTC | 9000 |
| TGGCAAGAAC GTCACCTACG AATGTAAGTG TGGTGACTAC | 9040 |
| AGCACAGGTA TTGTGAGCAC GCGAACGAAG ATGAACGGCT | 9080 |
| GCACTAAAGC AAAACAATGC ATTGCCTACA AGCGCGACCA | 9120 |
| AACGAAATGG GTCTTCAACT CGCCGGATCT TATTAGGCAC | 9160 |
| ACAGACCACT CAGTGCAAGG TAAACTGCAC ATTCCATTCC | 9200 |
| GCTTGACACC GACAGTCTGC CCGGTTCCGT TAGCTCACAC | 9240 |
| GCCTACAGTC ACGAAGTGGT TCAAAGGCAT CACCCTCCAC | 9280 |
| CTGACTGCAA CGCGACCAAC ATTGCTGACA ACGAGAAAAT | 9320 |
| TGGGGCTGCG AGCAGACGCA ACAGCAGAAT GGATTACAGG | 9360 |
| GACTACATCC AGGAATTTTT CTGTGGGGCG AGAAGGGCTG | 9400 |
| GAGTACGTAT GGGGCAACCA TGAACCAGTC AGAGTCTGGG | 9440 |
| CCCAGGAGTC GGCACCAGGC GACCCACATG GATGGCCGCA | 9480 |
| TGAGATCATC ATCCACTATT ATCATCGGCA TCCAGTCTAC | 9520 |
| ACTGTCATTG TGCTGTGTGG TGTCGCTCTT GCTATCCTGG | 9560 |
| TAGGCACTGC ATCGTCAGCA GCTTGTATCG CCAAAGCAAG | 9600 |
| AAGAGACTGC CTGACGCCAT ACGCGCTTGC ACCGAACGCA | 9640 |
| ACGGTACCCA CAGCATTAGC AGTTTTGTGC TGTATTCGGC | 9680 |
| CAACCAACGC TGAAACATTT GGAGAAACTT TGAACCATCT | 9720 |
| GTGGTTTAAC AACCAACCGT TTCTCTGGGC ACAGTTGTGC | 9760 |
| ATCCCTCTGG CAGCGCTTGT TATTCTGTTC CGCTGCTTTT | 9800 |
| CATGCTGCAT GCCTTTTTTA TTGGTTGCAG GCGTCTGCCT | 9840 |
| GGGGAAGGTA GACGCCTTCG AACATGCGAC CACTGTGCCA | 9880 |
| AATGTTCCGG GGATCCCGTA TAAGGCGTTG GTCGAACGTG | 9920 |
| CAGGTTACGC GCCACTTAAT CTGGAGATTA CGGTCGTCTC | 9960 |
| ATCGGAATTA ACACCCTCAA CTAACAAGGA GTACGTGACC | 10000 |
| TGCAAATTTC ACACAGTCGT TCCTTCACCA CAAGTTAAAT | 10040 |
| GCTGCGGGTC CCTCGAGTGT AAGGCATCCT CAAAAGCGGA | 10080 |
| TTACACATGC CGCGTTTTTG GCGGTGTGTA CCCTTTCATG | 10120 |

| | |
|---|---|
| TGGGGAGGCG CACAGTGCTT CTGTGACAGT GAGAACACAC | 10160 |
| AACTGAGTGA GGCATACGTC GAGTTCGCTC CAGACTGCAC | 10200 |
| TATAGATCAT GCAGTCGCAC TAAAAGTTCA CACAGCTGCT | 10240 |
| CTGAAAGTCG GCCTGCGTAT AGTATACGGC AATACCACAG | 10280 |
| CGCGCCTGGA TACATTCGTC AACGGCGTCA CACCAGGTTC | 10320 |
| CTCACGGGAC CTGAAGGTCA TAGCAGGGCC GATATCAGCA | 10360 |
| GCTTTTTCAC CCTTTGACCA TAAGGTCGTC ATTAGAAAGG | 10400 |
| GGCTTGTTTA CAACTACGAC TTCCCTGAGT ATGGAGCTAT | 10440 |
| GAACCCAGGA GCGTTCGGCG ATATTCAAGC ATCCTCTCTT | 10480 |
| GATGCCACAG ACATAGTAGC CCGCACCGAC ATACGGCTGC | 10520 |
| TGAAGCCTTC TGTCAAGAAC ATCCACGTCC CCTACACCCA | 10560 |
| AGCAGTATCA GGGTATGAAA TGTGGAAGAA CAACTCAGGA | 10600 |
| CGACCCCTGC AAGAAACAGC ACCATTCGGA TGTAAAATTG | 10640 |
| AAGTGGAGCC TCTGCGAGCG ACTAACTGTG CTTATGGGCA | 10680 |
| CATCCCTATC TCGATTGACA TCCCTGATGC AGCTTTTGTG | 10720 |
| AGATCATCTG AATCACCAAC AATTTTAGAA GTCAGCTGCA | 10760 |
| CAGTAGCAGA CTGCATTTAT TCTGCAGACT TTGGTGGTTC | 10800 |
| GCTAACACTA CAGTACAAAG CTAACAGAGA GGGACATTGT | 10840 |
| CCAGTTCACT CCCACTCCAC TACAGCTGTT TTGAAGGAAG | 10880 |
| CGACCACACA TGTGACTGCC ACAGCCATAA CACTACATTT | 10920 |
| TAGCACATCG AGCCCACAAG CAAATTTCAT AGTTTCGCTA | 10960 |
| TGGCGCAAGA AGACCACCTG CAATGCTGAA TGTAAACCAC | 11000 |
| CGGCCGACCA CATAATTGGA GAACCACATA AGGTCGACCA | 11040 |
| AGAATTCCAG GCGGCAGTTT CCAAAACATC TTGGAACTGG | 11080 |
| CTGCTTGCAC TGTTTGGGGG AGCATCATCC CTCATTGTTG | 11120 |
| TAGGACTTAT AGTGTTGGTC TGCAGCTCTA TGCTTATAAA | 11160 |
| CACACGTAGA TGACTGAGCG CGGACACTGA CATAGCGGTA | 11200 |
| AAAACTCGAT GTACTTCCGA GGAAGCGTGG TGCATAATGC | 11240 |
| CACGCGCCGC TTGACACTAA AACTCGATGT ATTTCCGAGG | 11280 |
| AAGCACAGTG CATAATGCTG TGCAGTGTCA CATTAATCGT | 11320 |
| ATATTACACT ACATATTAAC AACACTATAT CACTTTTATG | 11360 |
| AGACTCACTA TGGGTTTCTA ATACACACTA CACACATTTT | 11400 |
| ATTTAAAAAC ACTACACACA CTTTATAAAT TCTTTTATAA | 11440 |
| TTTTTCTTTT GTTTTTTATT TTGTTTTTAA AATTTCAAAA | 11480 |
| AAAAAAAAAA AA | 11492 |

(2) INFORMATION FOR SEQ ID NO:2:

(i) SEQUENCE CHARACTERISTICS:
        (A) LENGTH: 11464 base pairs
        (B) TYPE: Nucleic acid
        (C) STRANDEDNESS: Double
        (D) TOPOLOGY: Unknown (ii) SEQUENCE DESCRIPTION: SEQ ID NO:2:

```
ATGGGCGGCG CATGAGAGAA GCCCAAACCA ATAACTACCC              40
AAAATGGAGA AAGTTCACGT TGACATCGAG GAAGATAGTC              80
CCTTCCTCAG AGCATTACAA CGGAGCTTCC CGCAGTTTGA             120
GGTAGAAGCC AAGCAGGTCA CAGATAATGA CCATGCTAAC             160
GCCAGAGCGT TTTCGCATTT GGCATCGAAA TTGATCGAGA             200
CGGAGGTGGA ACCATCCGAT ACGATCCTAG ACATTGGAAG             240
TGCGCCTGCC CGCAGAATGT ATTCCAAGCA TAAGTACCAT             280
TGCATCTGTC CGATGAAATG TGCAGAAGAT CCGGACAGAC             320
TGTTTAAGTA TGCAGCCAAG CTGAAGAAGA ACTGTAAAGA             360
GATTACAGAT AAGGAACTGG ACAAGAAGAT GAAGGAGCTT             400
GCGGAAGTCA TGAGCGACCC TGATCTCGAA ACTGAAACGA             440
TTTGCCTTCA CGACGATGAA ACCTGTCGAT TTGAGGGTCA             480
AGTCGCAGTG TATCAGGATG TGTACGCGGT TGACGGACCG             520
ACGAGCCTTT ACCATCAGGC CAACAAAGGG GTCAGAGTCG             560
CCTATTGGAT AGGATTCGAC ACTACCCCTT TTATGTTTAA             600
GAACCTGGCT GGAGCATATC CCTCCTATTC GACCAACTGG             640
GCCGACGAGA CCGTGTTAAC GGCTCGTAAT ATAGGCTTGT             680
GCAGCTCCGA TGTGATGGAG CGGTCACGTA GAGGGATGTC             720
CATCCTCAGA AAGAAATTTT TAAAACCATC CAATAACGTC             760
TTGTTCTCTG TAGGATCTAC CATCTACCAC GAGAAGCGAG             800
ACTTACTAAG GAGTTGGCAC CTACCGTCCG TTTTTCACCT             840
ACGTGGTAAG CAGAATTACA CTTGTCGGTG TGAGACTATA             880
GTTAGTTGCG ACGGGTACGT CGTCAAAAGG ATAGCTATTA             920
GTCCAGGTCT GTACGGGAAA CCGTCGGGCT ACGCTGCCAC             960
GATGCATCGC GAGGGATTCT TGTGCTGCAA GGTGACGGAC            1000
ACGCTTGACG GGGAGAGGGT CTCTTTCCCC GTATGCACGT            1040
ACGTGCCAGC CACATTGTGC GACCAAATGA CAGGCATTCT            1080
GGCAACAGAT GTCAGTGCAG ACGACGCGCA GAAATTGCTG            1120
GTTGGGCTCA ACCAGCGAAT AGTCGTAAAT GGCCGCACTC            1160
AAAGGAATAC TAACACAATG AAGAACTATT TATTACCCGT            1200
CGTGGCACAA GCATTTGCCA GATGGGCTAA AGAGTACACA            1240
GAAGATCAAG AAGATGAAAG ACCATTGGGG CTTAGGGACC            1280
GCCAGTTGGT AATGGGGTGT TGTTGGGCGT TCAGGAAACA            1320
CAAGATAACA TCAGTGTACA AACGACCAGA CACCCAAACG            1360
ATCATCAAGG TAAACAGCGA TTTCCACTCT TTCGTGCTGC            1400
CCAGAATTGG AAGCAACACC TTGGAGATTG GGCTGAGGAC            1440
CAGGATCAGA AAACTACTGG AGGAACCTGT GGACAGACCA            1480
CCACTGATTA CCGCCGACGA CATACAGGAA GCCAAGAACG            1520
CGGCGGATGA GGCTAAGGAA GTCAAGGAGG CCGAAGAGCT            1560
```

-continued

```
CAGGGCAGCA TTACCACCGC TGTCTGCCGA TGTAGAGGAA           1600

CCTGCACTGG AGGCGGACGT TGACTTAATG CTGCAGGAGG           1640

CGGGAGCAGG ATCTGTCGAA ACCCCCAGGG GGCTCATCAA           1680

AGTCACCAGT TATGCAGGAG AAGACAAAAT TGGCTCTTAT           1720

GCGGTGCTCT CCCCACAAGC AGTACTGCGA AGTGAAAAAC           1760

TGACGTGCAT CCACCCGCTT GCAGAGCAAG TAATTGTAAT           1800

CACACACTCT GGAAGGAAGG GTAGATACGC AGTTGAGCCT           1840

TACCACGGAA AAGTGGTAGT ACCCGAAGGG CAAGCTATAC           1880

CTGTCCAAGA CTTCCAAGCA CTCAGTGAGA GCGCCACAAT           1920

TGTGTACAAC GAACGTGAGT TCGTGAATAG GTATTTACAC           1960

CACATTGCCA CGCACGGTGG AGCTCTGAAC ACAGACGAGG           2000

AGTATTACAG AGTGGTGAAA CCTAGTGAAC ATGAAGGTGA           2040

GTACTTATAT GACATTGACA AGAAACAATG TGTGAAGAAA           2080

GAACTGGTTA CGGGACTAGG TTTGACAGGA GAACTTGTCG           2120

ATCCCCCCTT CCATGAATTT GCATATGAAA GCTTGAGGAC           2160

ACGTCCGCCC GCACCTTATC AAGTACCAAC TATAGGTGTG           2200

TATGGCGTTC CCGGGTCCGG GAAGTCTGGA ATTATTAAGA           2240

GCGCAGTCAC AAAGAAGGAC TTGGTAGTGA GTGCTAAGAA           2280

GGAGAACTGC GCCGAGATAA TAAGGGACGT CAAGAAGATG           2320

AAAGGGCTAG ACGTCAATGC CCGGACGGTG GACTCAGTGC           2360

TGTTAAATGG ATGCAAGCAC CCGGTCGAGA CTTTGTACAT           2400

TGATGAAGCC TTTGCATGCC ACGCCGGCAC TCTCAGGGCC           2440

TTAATAGCCA TTATACGCCC AAAGAAAGCA GTGCTATGTG           2480

GTGACCCAAA GCAATGTGGC TTCTTCAACA TGATGTGCCT           2520

GAAAGTGCAC TTCAACCATG AAATATGCAC TCAAGTTTTC           2560

CACAAAAGCA TATCTCGCAG GTGTACCAAG TCAGTGACGT           2600

CGGTAGTGTC CACACTGTTT TATGACAAAA GAATGAGAAC           2640

TACTAACCCA AGGGATTCCA AAATCGAAAT TGACACAACA           2680

GGAAGTACTA AACCAAAAAA GGATGACTTG ATTCTCACAT           2720

GTTTTAGGGG ATGGGTTAAG CAACTGCAAA TAGACTACAA           2760

AGGAAATGAA ATAATGACCG CGGCTGCCTC ACAGGGATTG           2800

ACGCGGAAAG GTGTCTATGC AGTTAGGTAC AAAGTTAACG           2840

AGAACCCATT GTACGCACCC ACCTCAGAGC ATGTAAATGT           2880

GCTGTTGACC CGGACGGAAG ACAAGATTGT GTGGAAGACT           2920

CTTGCAGGGG ACCCGTGGAT AAAGACCCTG ACCGCGAAGT           2960

ACCCCGGAGA TTTCACTGCA ACAATGGAAG AATGGCAGGC           3000

AGAACATGAT GCCATCATGA GACACATCCT GGAGAAACCG           3040

GATCCCACGG ATGTCTTCCA AAATAAAGCT AATGTTTGCT           3080

GGGCAAAGGC ACTTGTACCT GTGCTTAAGA CAGCCGGGAT           3120
```

```
AGATTTGACC ACAGAGCAGT GGAACACAGT GGATTACTTC            3160

AAAGAGGATA AGGCCCACTC AGCTGAGATT GTCCTGAATC            3200

AGCTGTGCGT GCGATTCTTC GGTCTAGACT TAGATTCTGG            3240

TTTGTTTTCC GCCCCCACAG TTCCACTCTC CATTAGGAAC            3280

AACCATTGGG ACAACTCACC GTCACCCAAC ATGTACGGGT            3320

TGAATCAAGA AGTGGTCAGG CAACTATCAC GCAGGTACCC            3360

TCAATTACCA CGTGCGGTGA CTACTGGGAG AGCATACGAC            3400

ATGAACACCG GTACTTTGCG CAATTATGAT CCGCGCATAA            3440

ATTTAGTACC GGTGAACCGT CGTCTACCAC ATGCTCTCGT            3480

GACGCAACAT GCTGATCATC CTCCCAGTGA TTTTTCCGCC            3520

TTTGTCAGTA AGCTTAAAGG CAGAACGGTC CTAGTAGTTG            3560

GTGAGAAGAT GAGTATTTCA GGTAAGACGG TAGACTGGTT            3600

ATCTGAAACA CCTGATTCTA CTTTTAGGGC GCGCCTAGAT            3640

CTAGGCATAC CCAATGAACT ACCGAAGTAC GATATCGTCT            3680

TCGTAAATGT AAGAACACAG TACCGCTACC ACCACTACCA            3720

GCAGTGTGAG GACCACGCCA TTAAGTTGAG CATGTTGACC            3760

AAGAAGGCCT GCCTGCACCT GAACCCCGGA GGAACCTGTG            3800

TGAGCATTGG TTACGGCTAT GCGGACCGGG CCAGTGAAAG            3840

CATCATAGGT GCAGTTGCTC GGCAGTTCAA GTTCTCGAGG            3880

GTATGCAAAC CGAAGGTGTC TAAGGAGGAG ACCGAAGTGC            3920

TATTTGTCTT CATTGGGTTC GATCGTAAAA CGCGAACCCA            3960

TAACCCATAC AAGCTCTCCT CCACCCTGAC CAATATTTAC            4000

ACCGGCTCGA GGCTCCATGA AGCTGGCTGC GCACCTTCGT            4040

ATCATGTAGT GCGCGGGGAT ATAGCCACTG CCACGGAAGG            4080

AGTAATCGTT AATGCTGCCA ACAGCAAGGG CCAGCCAGGC            4120

AGTGGAGTGT GCGGAGCTCT GTACCGGAAG TACCCCGAAA            4160

GCTTCGATTT ACAACCAATA GAAGTGGGGA AAGCTAGATT            4200

GGTCAAAGGT AACTCAAAAC ATCTCATTCA TGCAGTGGGG            4240

CCGAATTTTA ACAAAGTGTC TGAAGTGGAA GGTGACAAAC            4280

AGCTGGCAGA AGCGTATGAA TCTATAGCCA GGATTATTAA            4320

TGACAACAAT TATAGATCTG TGGCTATTCC GCTTCTGTCC            4360

ACTGGAATAT TTGCCGGAAA CAAGGATAGG TTAATGCAAT            4400

CCTTAAACCA TCTGTTAACG GCATTGGACA CAACAGACGC            4440

AGATGTGGCC ATATACTGCA GAGACAAGAA ATGGGAAGTG            4480

ACGTTGAAAG AGGTCGTAGC CAGGAGAGAG GCGGTAGAGG            4520

AGATATGTAT CTCCGAAGAT TCCTCCGTAG CAGAGCCGGA            4560

TGCAGAGCTG GTTAGAGTTC ACCCTAAGAG CTCTTTGGCT            4600

GGAAGGAAAG GTTACAGCAC TAGCGATGGG AAGACATTCT            4640

CATATCTTGA AGGAACCAAA TTTCATCAGG CGGCGAAGGA            4680

CATGGCAGAA ATTAACGCTA TGTGGCCTGC CGCTACAGAG            4720
```

| | |
|---|---|
| GCTAATGAGC AGGTGTGCTT ATACATTCTG GGTGAAAGTA | 4760 |
| TGAGCAGTAT AAGATCCAAA TGCCCCGTTG AGGAGTCAGA | 4800 |
| GGCATCCACC CCACCAAGTA CATTGCCTTG CTTGTGCATC | 4840 |
| CACGCTATGA CCCCGGAACG GGTTCAGCGT TTGAAAGCCT | 4880 |
| CCCGCCCCGA ACAAATTACA GTTTGTTCTT CCTTCCCATT | 4920 |
| GCCGAAGTAC AGAATAACAG GAGTGCAGAA GATTCAATGT | 4960 |
| TCGCATCCTA TACTTTTCTC TCCTAAAGTA CCTGAGTACA | 5000 |
| TACACCCTAG AAAGTACCTT GCAGACGCAG CTTCCGCAAA | 5040 |
| CAATGGGGCA GCCGAATCAA CATCGGTGGA CGTGCAGCCA | 5080 |
| CAGCTGGAAG AGAGTCCTGA GAACACGGAA CAACTGGTGG | 5120 |
| AGGAGGAAGA CAGTATAAGC GTGCTGTCTG AGGATACACC | 5160 |
| ACACCAAGTG CACCAAGTGG AGGCTGAAGT GCATCGCTTC | 5200 |
| AGCGCAAGTG CTCAATCTTC GTCCTGGTCC ATTCCACGTG | 5240 |
| CATCCGACTT TGATGTCGAG AGTCTTTCCG TGCTCGAATC | 5280 |
| CCTGGGTGCT AATGATACAA TCAGCATGGA GTCGTCCTCA | 5320 |
| AACGAAACAG CTCTTGCTTT GCGGACCATT TTTAAGACTC | 5360 |
| CACCCATTCC AAGGCCTCGA GTGCAGAGCA CATCCACAGA | 5400 |
| CGTGGTTAGT ATCTCAGCAC TCGAGTCTTG TGACAGCACC | 5440 |
| AGCGATGCGC GTAGCATAGA CTCGGATGAA ACCGATGTTT | 5480 |
| CCATCTTTGA CAAAAGGTTG GAGTTCCTGG CCAGACCTGT | 5520 |
| TCCCGCACCG CGAACCAAAT TTAGGACTCC ACCCGTCCCG | 5560 |
| AAACCGCGTG CGCGGAGGCC ATTACATCCT TTGTCTAGTA | 5600 |
| GATCAAGCTC GCGCTCTAGC CTGGCGTCTA ATCCACCAGG | 5640 |
| TGTTAACCGA GTGATCACTA GGGAAGAATT TGAGTCCTTC | 5680 |
| GTTGCCCAAC AGCAATGACG GTTCGACGCG GGCGCGTACA | 5720 |
| TTTTCTCCTC GGATACTGGT CAAGGACATT TGCAACAAAA | 5760 |
| ATCAGTAAGG CAGACAGTAT TGTCTGAAGT GGTGCTAGAG | 5800 |
| AGGACTGAGT TAGAGATCTC GTACGCCCCG CGCCTCGACC | 5840 |
| TGAACAAAGA AGAAATACTG AGAAAGAAGT TACAACTGAA | 5880 |
| CCCTACGCAA GCTAACCGGA GTAGATATCA GTCACGGAGG | 5920 |
| GTTGAAAACA TGAAGGCCAT AACAACTAAG AGAATCTTAC | 5960 |
| AGGGATTAGG TCACTACCTG AAATCTGAAG GCAAGGTGGA | 6000 |
| GTGCTATCGT ACGTTGCACC CCGTACCTTT GTATTCAGCA | 6040 |
| AGTGTGAACA GAGCGTTCTC CAGTCCCAAA GTTGCTGTTG | 6080 |
| AAGCATGTAA CGTTGTTCTG AAGGAAAATT TTCCGACAGT | 6120 |
| GGCGTCGTAC TGCATAATAC CTGAGTACGA CGCCTACTTG | 6160 |
| GACATGGTGG GCGGTGCATC ATGTTGCTTG GATACGGCGA | 6200 |
| GTTTTTGCCC TGCCAAGTTG CGTAGCTTTC CGAAGAAACA | 6240 |
| CGCATACCTC GAGCCCACCA TTCGGTCTGC AGTCCCATCA | 6280 |

| | |
|---|---|
| GCAATTCAGA ACACGCTGCA AAATGTACTC GCAGCTGCCA | 6320 |
| CAAAGAGAAA CTGCAATGTG ACTCAAATGA GGGAGCTGCC | 6360 |
| TGTACTGGAT TCTGCGGCCT TCAATGTAGA GTGTTTTAAA | 6400 |
| AAATACGCTT GCAATAATGA GTATTGGAG ACCTACAAGA | 6440 |
| AGAATCCTAT TAGATTGACC GAGGAAAATG TGGTCAACTA | 6480 |
| TATAACCAAG TTAAAAGGGC CGAAGGCGGC TGCCCTGTAT | 6520 |
| GCAAAGACTC ATAATTTAGA CATGCTGCAA GACATACCCA | 6560 |
| TGGACAGGTT TATTATGGAT TTAAAAAGAG ATGTCAAGGT | 6600 |
| AACTCCAGGA ACCAAGCATA CCGAAGAAAG GCCTAAGGTC | 6640 |
| CAAGTAATCC AGGCTGCAGA TCCATTGGCT ACAGCATACC | 6680 |
| TATGTGGGAT TCATAGAGAA TTGGTGCGCA GACTGAACGC | 6720 |
| AGTTCTGTTG CCCAACATAC ACACATTATT TGACATGTCT | 6760 |
| GCTGAGGATT TCGACGCCAT AATTGCCGAG CACTTCCAAC | 6800 |
| CAGGCGATTG GGTGTTAGAG ACAGACATAG CGTCATTCGA | 6840 |
| TAAAAGCGAA GATGACGCGA TGGCTCTGAC GGCACTGATG | 6880 |
| ATCCTGGAAG ACCTCGGGGT GGACCCAGAG CTGTTGACCC | 6920 |
| TAATCGAAGC GGCATTTGGC GAAATATCCT CCATTCACTT | 6960 |
| ACCAACCAAA ACTAAATTTA GGTTTGGAGC CATGATGAAA | 7000 |
| TCAGGGATGT TCTTGACTCT GTTTGTCAAT ACTGTGATCA | 7040 |
| ATATGGTCAT AGCTAGCAGA GTTCTGCGTG AGAGACTGAC | 7080 |
| AAACTCCCCT TGCGCCGCGT TCATTGGCGA CGACAATATC | 7120 |
| GTGAAAGGGG TTAAGTCCGA CAAACTCATG GCCGATAGGT | 7160 |
| GCGCTACATG GTTGAACATG GAAGTCAAAA TCATCGACGC | 7200 |
| AGTGGTTGGC GAGAAAGCTC CCTACTTCTG TGGTGGGTTT | 7240 |
| ATTTTATGTG ACTCTGTGAC CGGAACTGCA TGCCGTGTAG | 7280 |
| CAGACCCTTT GAAGAGATTA TTTAAGCTTG GAAAACCACT | 7320 |
| GGCTGTGGAT GATGAACATG ATGATGACAG GCGTCGAGCA | 7360 |
| CTACAGGAGG AATCTGCCCG GTGGAACCGG GTGGGAATTT | 7400 |
| TTTCCGAGCT GTGCAAAGCC GTCGAGTCGC GATATGAAAC | 7440 |
| AGTGGGCACG GCTGTCATTA TCATGGCCAT GACTACGCTC | 7480 |
| GCCAGCAGTG TCGAGTCGTT CAGTTGTCTA AGAGGGGCTT | 7520 |
| CTATATCCCT CTACGGCTAA CCTGAATGGA CTGCGACGTA | 7560 |
| GTCAAGTCCG CCGAAATGTT TCCTTATCAA CCAATGTACC | 7600 |
| CAATGCAGCC CATGCCCTTC CGCAACCCTT TTGCGACTCC | 7640 |
| CAGAAGACCA TGGTTTCCAA GGACCGACCC CTTTTTAGCG | 7680 |
| ATGCAGGTGC AAGAGCTGGC AAGGTCCATG GCCAACTTGA | 7720 |
| CGTTCAAGCA ACGGCGAGAT GTGCCGCCCG AGGGTCCACC | 7760 |
| GGCTAAGAAG AAGAAGAAGG ACAACTGCA ACAAGGTGGT | 7800 |
| CGGAATCAGA ATGGAAAGAA AAGAACAAG CTAGTAAAGA | 7840 |
| AAAAGAAGAA GACAGGGCCA CCACCCCCAA AAAATACTGG | 7880 |

| | |
|---|---|
| TGGCAAAAAG AAAGTCAATA GGAAGCCAGG GAAGAGACAA | 7920 |
| CGAATGGTTA TGAAGTTGGA GTCAGACAAG ACATTCCCTA | 7960 |
| TCATGCTAGA TGGAAAAGTT AATGGATATG CATGCGTGGT | 8000 |
| CGGTGGCAAG CTGTTTAGAC CACTGCATGT GGAGGGTAAG | 8040 |
| ATTGACAATG ACGTGTTGTC CTCCCTCAAG ACCAAAAAGG | 8080 |
| CATCTAAGTA TGATCTGGAG TATGCTGATG TGCCGCAGAG | 8120 |
| CATGCGCGCA GACACATTTA AATACACTCA TGAAAAACCC | 8160 |
| CAGGGCTATT ACAGCTGGCA CCATGGAGCA GTACAGTATG | 8200 |
| AAAATGGCAG ATTCACAGTG CCCAAAGGAG TCGGAGCCAA | 8240 |
| AGGAGATAGC GGTCGCCCCA TACTTGACAA CCAAGGGCGT | 8280 |
| GTGGTCGCTA TTGTGCTTGG CGGAGTGAAT GAAGGCTCCA | 8320 |
| GAACGGCACT GTCTGTCGTG ACGTGGAACG AAAAAGGGGT | 8360 |
| TACAGTCAAA TACACCCCCG AGAATAGCGA GCAGTGGTCC | 8400 |
| CTGGTGACCA CCATGTGCCT GCTAGCCAAT GTCACGTTCC | 8440 |
| CGTGCACCCA ACCACCCATC TGCTACGACC GTAAGCCAGC | 8480 |
| AGAGACTTTG TCCATGCTCA GTCATAACAT AGACAATCCT | 8520 |
| GGTTATGACG AGTTGCTCGA AGCAGTACTG AAATGTCCAG | 8560 |
| GCAGAGGCAA GAGGTCCACG GAGGAGCTGT TTAAGGAGTA | 8600 |
| CAAGTTAACA CGCCCGTACA TGGCCAGGTG CATCAGGTGT | 8640 |
| GCGGTCGGAA GTTGCCACAG CCCCATAGCC ATAGAGGCGG | 8680 |
| TAAGGAGCGA AGGGCACGAT GGCTATGTAC GACTCCAGAC | 8720 |
| CTCATCTCAG TATGGATTAG ACCCATCAGG AAACTTGAAA | 8760 |
| GGCAGAACCA TGAGGTATGA TATGCATGGA ACCATAGAAG | 8800 |
| AGATACCGTT GCATCAGGTG TCTGTTCATA CCTCACGTCC | 8840 |
| TTGCCACATA ATAGATGGGC ATGGATACTT TCTGCTTGCC | 8880 |
| AGGTGCCCTG CAGGAGACTC CATAACTATG GAATTTAAGA | 8920 |
| AAGAATCAGT CACCCATTCC TGCTCTGTGC CCTACGAAGT | 8960 |
| AAAGTTTAAT CCTGCGGGAA GAGAACTGTA CACACACCCA | 9000 |
| CCAGAGCACG GAGCTGAACA ACCTTGTCAC GTGTACGCTC | 9040 |
| ACGACGCACA AAATAGGGGA GCTTACGTGG AAATGCACCT | 9080 |
| TCCAGGATCC GAAGTGGACA GTACTTTACT GTCCATGAGC | 9120 |
| GGTAGTTCTG TTCATGTGAC TCCACCTGCC GGGCAAAGCG | 9160 |
| TCCAAGTGGA ATGCGAATGT GGTGGCACCA AGATCTCTGA | 9200 |
| AACCATCAAT TCAGCTAAAC AATACAGTCA GTGCTCAAAG | 9240 |
| ACATCTCAGT GCAGGGCATA CCGTACACAG AATGACAAAT | 9280 |
| GGGTGTACAA TTCGGATAAA CTGCCTAAAG CATCGGAGA | 9320 |
| AACTCTCAAA GGCAAATTGC ATGTGCCCTT CGTACTGACC | 9360 |
| GAAGCGAAAT GCACAGTACC ATTGGCTCCA GAACCCATTA | 9400 |
| TCACCTTTGG GTTCCGCTCT GTGTCTCTGA AACTTCATCC | 9440 |

| | |
|---|---|
| TAAGAACCCC ACCTTCCTAA CCACGAGGCA GCTGGATGGA | 9480 |
| GAACCAGCTT ACACCCACGA ACTTATAACC CACCCTGTGG | 9520 |
| TGAGAAATTT CTCGGTTACA GAGAAAGGTT GGGAATTTGT | 9560 |
| GTGGGGAAAC CATCCGCCTC AAAGGTACTG GTCTCAAGAA | 9600 |
| ACTGCACCAG GTAATCCACA CGGACTACCA CACGAGGTGA | 9640 |
| TCACGCATTA CTATCACAGA TATCCCATGT CCACCATCCT | 9680 |
| CGGCTTATCA ATCTGTGCGG CGATAGTGAC GACATCCATT | 9720 |
| GCGGCATCCG TATGGCTGTT TTGCAAATCA CGGATTTCAT | 9760 |
| GCCTGACCCC CTATCGCTTG ACTCCGAATG CCAGCATGCC | 9800 |
| TCTGTGCTTA GCCGTCTTGT GCTGCGCACG CACAGCCAAA | 9840 |
| GCCGAAACTA CTTGGGAATC CCTAGATCAC CTCTGGAACC | 9880 |
| ACAACCAGCA GATGTTCTGG AGTCAGCTGC TAATCCCGCT | 9920 |
| AGCAGCACTG ATAGTTGCTA CCCGCTTGCT GAAATGTGTG | 9960 |
| TGTTGCGTTG TGCCTTTTTT AGTCGTGGCC GGCGCCGTAG | 10000 |
| GCGCCGGCGC TTACGAGCAC GCGACTACGA TGCCGAACCA | 10040 |
| AGTGGGGATC CCGTATAATA CCATTGTCAA CAGAGCGGGT | 10080 |
| TATGCACCTC TACCTATTAG CATAGTACCT ACTAAAGTGA | 10120 |
| AGCTGATTCC AACAGTGAAT CTTGAGTACA TTACATGCCA | 10160 |
| TTACAAGACT GGAATGGATT CACCCGCCAT TAAATGCTGC | 10200 |
| GGCACTCAGG AGTGTTCTCC AACTTACAGG CCGGACGAGC | 10240 |
| AATGCAAAGT CTTCTCTGGA GTATACCCAT TTATGTGGGG | 10280 |
| AGGGGCGTAT TGCTTTTGCG ATACGGAGAA TACCCAGATA | 10320 |
| AGCAAGGCGT ACGTGACGAA ATCGGAAGAT TGCGTCACCG | 10360 |
| ATCACGCCCA GGCATACAAA GCACATACAG CCTCAGTCCA | 10400 |
| AGCCTTCTTA AATATTACAG TTGGAGGACA CTCAACGACA | 10440 |
| GCAGTGGTGT ATGTGAATGG AGAGACTCCC GTTAATTTTA | 10480 |
| ATGGAGTGAA GCTGACCGCG GGCCCTCTGT CCACAGCCTG | 10520 |
| GTCGCCGTTC GACAAGAAGA TCGTGCAGTA CGCCGGGGAA | 10560 |
| ATTTATAACT ATGACTTTCC GGAATATGGA GCCGGCCACG | 10600 |
| CAGGAGCGTT TGGTGACATC CAGGCTAGGA CGGTATCTAG | 10640 |
| TTCCGATGTA TACGCCAACA CAAACCTTGT GCTGCAGAGA | 10680 |
| CCCAAAGCCG GAGCGATCCA TGTCCCGTAC ACCCAGGCCC | 10720 |
| CATCTGGGTA TGAACAATGG AAGAAAGATA AACCACCATC | 10760 |
| CCTCAAGTTC ACAGCCCCGT TCGGTTGTGA AATTTACACC | 10800 |
| AACCCTATCC GTGCTGAAAA CTGCGCTGTG GGATCAATTC | 10840 |
| CGCTAGCTTT TGACATTCCC GATGCTCTGT TTACCAGGGT | 10880 |
| GTCCGAAACA CCGACATTAT CTGCTGCCGA GTGCACTCTG | 10920 |
| AACGAGTGTG TATATTCATC CGACTTTGGC GGGATCGCTA | 10960 |
| CAGTCAAATA CTCGGCGAGC AAGTCAGGCA AATGTGCAGT | 11000 |
| TCATGTACCC TCAGGCACGG CTACATTGAA AGAAGCCGCA | 11040 |

| | |
|---|---|
| GTCGAGTTGG CCGAACAGGG TTCGGCTACT ATACATTTTT | 11080 |
| CGACTGCCAG CATTCATCCG GAGTTTAGAC TCCAGATATG | 11120 |
| CACGTCTTAC GTTACGTGCA AAGGGGATTG TCACCCTCCG | 11160 |
| AAAGATCACA TTGTGACGCA TCCCCAATAC CACGCCCAGT | 11200 |
| CATTTACAGC TGCGGTATCA AAAACCGCTT GGACGTGGTT | 11240 |
| AACATCCTTA CTGGGAGGGT CAGCTATAAT TATAATAATT | 11280 |
| GGACTTGTGT TAGCCACAGT TGTGGCTATG TATGTGCTGA | 11320 |
| CCAACCAGAA ACATAATTAG TATTAGCAGC GATTGGCATG | 11360 |
| CTGCTTGTAA AGTTTTATTA CAAATAACGT GCGGCAATTG | 11400 |
| GCGAGCCGCT TTAATTAGAA TTTTATTTTC TTTTACCATA | 11440 |
| ATTGGATTTT GTTTTTAATA TTTC | 11464 |

(2) INFORMATION FOR SEQ ID NO:3:

(i) SEQUENCE CHARACTERISTICS:
        (A) LENGTH: 4003 base pairs
        (B) TYPE: Nucleic acid
        (C) STRANDEDNESS:Double
        (D) TOPOLOGY: Unknown (ii) SEQUENCE DESCRIPTION: SEQ ID NO:3:

| | |
|---|---|
| CCCAGTAACT CTCTACGGCT GACCTGAATG GACTGTAACG | 40 |
| TAGTTCAGTC CGCAACCATG TTCCCTTACC AATCACCAAT | 80 |
| GTTTCCAATG CAACCAGCGC CTTTTCGCAA CCCGTACGCT | 120 |
| CCTCCTAGAA GACCGTGGTT CCCTAGAACC GATCCCTTCT | 160 |
| TAGCCATGCA GGTGCAGGAG TTGGCCCGAT CAATGGCGAG | 200 |
| CTTGACGTTT AAACAGCGTC GAGATACGCC ACCCGAGGGG | 240 |
| CCACCTGCTA AGAAGAAGCG TAAGGAGCCT CAACAGCAGG | 280 |
| TAGCTCAGGC GCAGGTTAAG AAAAAGAACG GAAAACCGAA | 320 |
| GAAGAAGAAA AGTAACGGAG CACCACCCCC AAAAAATCAG | 360 |
| AAGAGCACCA AGAAGAAGAC CAATAAGAAA CCTGGAAAAA | 400 |
| GACAACGGAT GGTTATGAAG TTAGAATCAG ACAAAACATT | 440 |
| TCCTATTTTG CTGGATGGAA AAATTAATGG ATATGCTTGC | 480 |
| GTTGTTGGAG GAAAGCTATT TCGACCCATG CACGTGGAAG | 520 |
| GCAAAATTGA CAATGAAACT CTTGCCTCCC TGAAGACGAA | 560 |
| GAAGGCATCC AAATACGACC TAGAGTATGC CGATGTTCCT | 600 |
| CAAAGCATGC GAGCAGATAC CTTTAAATAC ACACATGATA | 640 |
| AGCCTCAAGG GTATTATAAT TGGCATCACG GCGCCGTGCA | 680 |
| GTATGAAAAT GGGAGATTCA CGGTGCCGAA AGGTGTGGGA | 720 |
| GCGAAAGGAG ACAGTGGACG CCCCATACTA GATAATCAAG | 760 |
| GCAGAGTCGT GGCCATTGTG CTGGGAGGGG TGAATGAAGG | 800 |
| ATCCAAGACA GCTTTGTCCG TAGTTATGTG GAATGAAAAA | 840 |
| GGGGTCACCG TAAAATATAC ACCAGAAAAC TGTGAGCAAT | 880 |
| GGTCACTAGT TACCACCATG TGTCTTCTCG CCGATGTTAC | 920 |

| | |
|---|---|
| GTTCCCTTGT TCCACTCCAC CAATTTGCTA CGACCGAGCA | 960 |
| CCCGCAGAAA CCCTGATGAT GCTTAGCAAG AACATTGACA | 1000 |
| ATCCTGGCTA TGATGAATTG CTGGAAGCAG TGCTGAAATG | 1040 |
| CCCCGGCAGA CAGAAGAGAT CTACGGAGGA GTTATTTAAG | 1080 |
| GAGTACAAAC TTACACGTCC GTACATGGCC AAGTGTGTGC | 1120 |
| GGTGTGCCGT TGGAAGTTGC CACAGCCCGA TCGCTATAGA | 1160 |
| AGCAGTAAGA AGCGACGGGC ATGACGGCTA CATCCGAATA | 1200 |
| CAGACATCAT CACAGTACGG TTTAGACCCC TCCGGGAACG | 1240 |
| TTAAGAGCAG AGTTATGAGG TATAATCTGT ATGGCAAGAT | 1280 |
| CGTAGAAGTT CCATTACATC AGGTTTCATT ACACACATCT | 1320 |
| CGGCCTTGCC ACATTATTGA TGGTCACGGA TATTTCCTCC | 1360 |
| TCGCACGCTG CCCAGAGGGC GACTCTATCA CCATGGAGTT | 1400 |
| TAAGAAGGAT TCCGTCACCC ATTCCTGTTC AGTGCCTTAT | 1440 |
| GAAGTGAAAT TCACACCCGT GGGCAGAGAA TTATATAGCC | 1480 |
| ATCCCCCAGA ACACGGCACA GAACATCCGT GCCGTGTGTA | 1520 |
| TGCCCACGAC GCCCAGCAAA AGATGCGTA TGTGGAGATG | 1560 |
| CACCTGCCCG GTCCGAAGT TGACAGTTCC CTGCTCTCCA | 1600 |
| TGAGCGGTAG TGCGGTCCGG GTAACACCAC CATCAGGGCA | 1640 |
| AAGTGTCCTT TGGAGTGCA ACTGTGGCTC CGCTGTGTCG | 1680 |
| GAAACCATAA ACACTGCAAA ATCATACAGC CAATGCACAA | 1720 |
| AAACATCACA ATGCCGCGCG TACCGTCTGC AGAATGATAA | 1760 |
| GTGGGTATAC AATTCAGACA AACTTCCAAA GGCATCGGGA | 1800 |
| GAAACGCTGA AGGGAAACT GCATGTACCT TATCTCCTTT | 1840 |
| CCGAAGCGAA GTGTACCGTA CCTTTAGCAC CCGAGCCAAT | 1880 |
| AGTAACCTTC GGCTTTCGAT TCGTATCTTT GAAATTGCAT | 1920 |
| CCACGGAATC CGACATATTT GACTACCCGC CAGCTAGATG | 1960 |
| GAGAACCGAA TTACCCCAC GAGCTAATTT CAGAGCCAAC | 2000 |
| AACTAGAAAT TTTACAGTGA CTGAGCATGG ATGGGGATAC | 2040 |
| GTTTGGGGTA ATCACCCGCC TCAGAGGTAC TGGGCACAGG | 2080 |
| AGACAGCTCC AGGCAACCCG CATGGGCTGC CGCACGAGGT | 2120 |
| GATTACTCAT TACTATAACA GGTACCCAAT GTCCACGATT | 2160 |
| TTCGGACTAT CGATTTGCGC CGCAGTGGTA ACCACCTCAA | 2200 |
| TAGCCGCATC CACCTGGCTG TTGTGCAAGT CGAGAGTATC | 2240 |
| TTGTTTGACT CCGTATCGAC TGACCCCGAA TGCTCAGTTA | 2280 |
| CCTGTGTGTC TAGCCTTCCT GTGCTGCGCG AGGACAGCCC | 2320 |
| GTGCAGAGAC CACATGGGAA TCACTAGACC ATTTATGGAA | 2360 |
| CCATAATCAA CAGATGTTCT GGAGTCAACT GCTCATTCCC | 2400 |
| CTAGCCGCGC TCATTGTGGT GACCCGCTTG CTGAAGTGCA | 2440 |
| TGTGTTGCGT CGTTCCTTTT TTAGTCCTAG CAGGCGCCGC | 2480 |

| | |
|---|---|
| AAGCGTCGGC GCCTACGAAC ACGCAACCAC GATGCCGAAT | 2520 |
| CAGGTGGGGA TCCCGTATAA TACAGTAGTC AACCGCGCAG | 2560 |
| GTGACGCACC ATTGGCAATC AGCATTATTC CAACCAAGAT | 2600 |
| ACGGCTAATT CCTACTTTGA ATTTAGAATA TATTACATGC | 2640 |
| CACTATAAGA CAGGATTAGA TTCACCTTTC ATTAAATGCT | 2680 |
| GCGGAACGCA GGAATGCCCC CAAGTGAATA GACCCGATGA | 2720 |
| ACAGTGTAAA GTCTTCACGG GGGTGTATCC GTTTATGTGG | 2760 |
| GGAGGCGCCT ACTGCTTCTG TGACTCTGAA ACACGCAAA | 2800 |
| TTAGTCGAGC GTATGTGATG AAATCAGATG ACTGCTCAGC | 2840 |
| TGACCACGCC TTGGCCTACA AGCTCATAC TGCCTCAGTC | 2880 |
| CAAGCTTTTC TGAATATAAC TGTGGGAGAG CAATCGACGA | 2920 |
| CAGCGGTAGT GTACGTGAAT GGAGAAACAC CGGTCAATTT | 2960 |
| TAACGGCATT AAATTGGTTG CAGGCCCTTT ATCAACTGCC | 3000 |
| TGGACCCCAT TTGATCGGAA AGTGGTGCAG TACGCCGGAG | 3040 |
| AGATCTACAA TTATGACTTC CCGGAGTACG GAGCTGGGCA | 3080 |
| TGCAGGGGCG TTCGGGGATC TTCAAGCCAG AACAATCACC | 3120 |
| AGTAATGACC TGTACGCCAA CACGAATTTA GTATTGCAAA | 3160 |
| GACCCAACAC AGGCACCATC CATGTTCCTT ACACGCAGGC | 3200 |
| ACCGTCAGGC TTTGAGCAGT GGAAGAAAGA CAAACCACCA | 3240 |
| TCATTAAAGT ACACCGCACC ATTTGGGTGC GAAATTCATG | 3280 |
| TGAATCCCGT CAGAGCTGAG AATTGCGCAG TAGGATTTAT | 3320 |
| ACCATTAGCC TTCGACATAC CCGATGCCTT GTTTACCAGG | 3360 |
| GTGTCAGAAA CACCGACGTT GTCGAGCGCT GAGTGCTCCT | 3400 |
| TGAATGAGTG TACATACTCA ACGGACTTTG GCGGGATCGC | 3440 |
| CACTGTCAAG TACTCGGCTA GTAAATCAGG CAAATGCGCA | 3480 |
| GTACATGTTC CCTCAGGCAC TGCAACTCTG AAAGAGTCAT | 3520 |
| TGGTGGAAGT GGTCGAACAA GGGTCAATGA CCCTTCACTT | 3560 |
| TTCGACCGCC AGTATACACC CAGAGTTTAA ATTGCAGATC | 3600 |
| TGTACGAAGG TACTCACATG TAAAGGCGAC TGTCATCCGC | 3640 |
| CTAAAGACCA TATTGTGACG CACCCCAGC ACCACGCCCA | 3680 |
| GACATTTACA GCTGCGGTAT CCAAGACCGC TTGGACGTGG | 3720 |
| TTAACGTCAC TCTTAGGAGG GTCAGCAGTA ATTATTATAA | 3760 |
| TTGGCCTTGT ATTAGCAACT GTTGTTGCTA TGTATGTGCT | 3800 |
| GACCAACCAG AAACATAATT AGACCACAGC AGCGATTGGA | 3840 |
| AAGCTGCCTA TTAGAAACAT GTAGCGGCAA TTGGCAAGCC | 3880 |
| GCCTATAAAT GTTTAGCAGC AATTGGCAAG CTGCATATAT | 3920 |
| AAATTACCTA GCGGCAATTG GCACGCCGCT TATAAAATTT | 3960 |
| TTATTTTCTT TTACCAATAA TTGGATTTTG TTTTTAATAT | 4000 |
| TTC | 4003 |

(2) INFORMATION FOR SEQ ID NO:4:

(i) SEQUENCE CHARACTERISTICS:
        (A) LENGTH: 46 base pairs
        (B) TYPE: Nucleic acid
        (C) STRANDEDNESS:Double
        (D) TOPOLOGY: Unknown (ii) SEQUENCE DESCRIPTION: SEQ ID NO:4:

```
GTCACCGCGG TAATACGACT CACTATAGAT AGGGCATGGT              40

ATAGAG                                                    46
```

(2) INFORMATION FOR SEQ ID NO:5:

(i) SEQUENCE CHARACTERISTICS:
        (A) LENGTH: 24 base pairs
        (B) TYPE: Nucleic acid
        (C) STRANDEDNESS:Double
        (D) TOPOLOGY: Unknown (ii) SEQUENCE DESCRIPTION: SEQ ID NO:5:

```
TCACCTTATT CTGGAACACA TCAG                                24
```

(2) INFORMATION FOR SEQ ID NO:6:

(i) SEQUENCE CHARACTERISTICS:
        (A) LENGTH: 21 base pairs
        (B) TYPE: Nucleic acid
        (C) STRANDEDNESS:Double
        (D) TOPOLOGY: Unknown (ii) SEQUENCE DESCRIPTION: SEQ ID NO:6:

```
TCGGAGGAAG GCTGATGAAA C                                   21
```

(2) INFORMATION FOR SEQ ID NO:7:

(i) SEQUENCE CHARACTERISTICS:
        (A) LENGTH: 29 base pairs
        (B) TYPE: Nucleic acid
        (C) STRANDEDNESS:Double
        (D) TOPOLOGY: Unknown (ii) SEQUENCE DESCRIPTION: SEQ ID NO:7:

```
TCGGATCCGA TGAGAAAATA TACGCTCCC                           29
```

(2) INFORMATION FOR SEQ ID NO:8:

(i) SEQUENCE CHARACTERISTICS:
        (A) LENGTH: 32 base pairs
        (B) TYPE: Nucleic acid
        (C) STRANDEDNESS:Double
        (D) TOPOLOGY: Unknown (ii) SEQUENCE DESCRIPTION: SEQ ID NO:8:

```
GACTGGATCC GCAAACCAGT CCTGTTCTCA GG                       32
```

(2) INFORMATION FOR SEQ ID NO:9:

(i) SEQUENCE CHARACTERISTICS:
        (A) LENGTH: 33 base pairs
        (B) TYPE: Nucleic acid
        (C) STRANDEDNESS:Double
        (D) TOPOLOGY: Unknown (ii) SEQUENCE DESCRIPTION: SEQ ID NO:9:

```
GCATGGATCC AGCATGATCG GAAATGTCTT GTC                      33
```

(2) INFORMATION FOR SEQ ID NO:10:

(i) SEQUENCE CHARACTERISTICS:
        (A) LENGTH: 29 base pairs
        (B) TYPE: Nucleic acid
        (C) STRANDEDNESS:Double
        (D) TOPOLOGY: Unknown (ii) SEQUENCE DESCRIPTION: SEQ ID NO:10:

| | |
|---|---|
| TCGGATCCAC CGCCAAAATG TTTCCATAC | 29 |

(2) INFORMATION FOR SEQ ID NO:11:

(i) SEQUENCE CHARACTERISTICS:
        (A) LENGTH: 23 base pairs
        (B) TYPE: Nucleic acid
        (C) STRANDEDNESS:Double
        (D) TOPOLOGY: Unknown (ii) SEQUENCE DESCRIPTION: SEQ ID NO:11:

| | |
|---|---|
| TCGGGATCCC CGGAACATTT GGC | 23 |

(2) INFORMATION FOR SEQ ID NO:12:

(i) SEQUENCE CHARACTERISTICS:
        (A) LENGTH: 21 base pairs
        (B) TYPE: Nucleic acid
        (C) STRANDEDNESS:Double
        (D) TOPOLOGY: Unknown (ii) SEQUENCE DESCRIPTION: SEQ ID NO:12:

| | |
|---|---|
| CTGCTTTTCA TGCTGCATGC C | 21 |

(2) INFORMATION FOR SEQ ID NO:13:

(i) SEQUENCE CHARACTERISTICS:
        (A) LENGTH: 43 base pairs
        (B) TYPE: Nucleic acid
        (C) STRANDEDNESS:Double
        (D) TOPOLOGY: Unknown (ii) SEQUENCE DESCRIPTION: SEQ ID NO:13:

| | |
|---|---|
| CGATGCGGCC GCTTTTTTTT TTTTTTTTG AAATTTTAAA | 40 |
| AAC | 43 |

(2) INFORMATION FOR SEQ ID NO:14:

(i) SEQUENCE CHARACTERISTICS:
        (A) LENGTH: 43 base pairs
        (B) TYPE: Nucleic acid
        (C) STRANDEDNESS:Double
        (D) TOPOLOGY: Unknown (ii) SEQUENCE DESCRIPTION: SEQ ID NO:14:

| | |
|---|---|
| CAGCGTGAAG TCATCGGTAA TGCTGCGTGA TGGACATTTC | 40 |
| AAG | 43 |

(2) INFORMATION FOR SEQ ID NO:15:

(i) SEQUENCE CHARACTERISTICS:
        (A) LENGTH: 40 base pairs
        (B) TYPE: Nucleic acid
        (C) STRANDEDNESS:Double
        (D) TOPOLOGY: Unknown (ii) SEQUENCE DESCRIPTION: SEQ ID NO:15:

CAGCGTGAAG TCATCGGTAA TGCTTGATGG ACATTTCAAG        40

(2) INFORMATION FOR SEQ ID NO:16:

(i) SEQUENCE CHARACTERISTICS:
        (A) LENGTH: 20 base pairs
        (B) TYPE: Nucleic acid
        (C) STRANDEDNESS:Double
        (D) TOPOLOGY: Unknown (ii) SEQUENCE DESCRIPTION: SEQ ID NO:16:

CTAAGAGGGG CCCCTATATC        20

(2) INFORMATION FOR SEQ ID NO:17:

(i) SEQUENCE CHARACTERISTICS:
        (A) LENGTH: 45 base pairs
        (B) TYPE: Nucleic acid
        (C) STRANDEDNESS:Double
        (D) TOPOLOGY: Unknown (ii) SEQUENCE DESCRIPTION: SEQ ID NO:17:

GCGGAATTCT AATACGACTC ACTATAGATG GGCGGCGCAT        40

GAGAG        45

(2) INFORMATION FOR SEQ ID NO:18:

(i) SEQUENCE CHARACTERISTICS:
        (A) LENGTH: 22 base pairs
        (B) TYPE: Nucleic acid
        (C) STRANDEDNESS:Double
        (D) TOPOLOGY: Unknown (ii) SEQUENCE DESCRIPTION: SEQ ID NO:18:

TGACCGCGGG ACCTCTGTCC AC        22

(2) INFORMATION FOR SEQ ID NO:19:

(i) SEQUENCE CHARACTERISTICS:
        (A) LENGTH: 18 base pairs
        (B) TYPE: Nucleic acid
        (C) STRANDEDNESS:Double
        (D) TOPOLOGY: Unknown (ii) SEQUENCE DESCRIPTION: SEQ ID NO:19:

AAGTGCATCG ATTCAGCG        18

(2) INFORMATION FOR SEQ ID NO:20:

(i) SEQUENCE CHARACTERISTICS:
        (A) LENGTH: 30 base pairs
        (B) TYPE: Nucleic acid
        (C) STRANDEDNESS:Double
        (D) TOPOLOGY: Unknown (ii) SEQUENCE DESCRIPTION: SEQ ID NO:20:

CTGAAATGTC CAGGATCCAC GGAGGAGCTG        30

(2) INFORMATION FOR SEQ ID NO:21:

(i) SEQUENCE CHARACTERISTICS:
        (A) LENGTH: 30 base pairs
        (B) TYPE: Nucleic acid
        (C) STRANDEDNESS:Double
        (D) TOPOLOGY: Unknown (ii) SEQUENCE DESCRIPTION: SEQ ID NO:21:

CAGCTCCTCC GTGGATCCTG GACATTTCAG                                                30

(2) INFORMATION FOR SEQ ID NO:22:

(i) SEQUENCE CHARACTERISTICS:
            (A) LENGTH: 45 base pairs
            (B) TYPE: Nucleic acid
            (C) STRANDEDNESS:Double
            (D) TOPOLOGY: Unknown (ii) SEQUENCE DESCRIPTION: SEQ ID NO:22:

GACTGCGGCC GCTTTTTTTT TTTTGAAATA TTAAAAACAA                                     40

AATCC                                                                           45

(2) INFORMATION FOR SEQ ID NO:23:

(i) SEQUENCE CHARACTERISTICS:
            (A) LENGTH: 22 base pairs
            (B) TYPE: Nucleic acid
            (C) STRANDEDNESS:Double
            (D) TOPOLOGY: Unknown (ii) SEQUENCE DESCRIPTION: SEQ ID NO:23:

CGAGAATCGA TGCACTTCAG CC                                                        22

(2) INFORMATION FOR SEQ ID NO:24:

(i) SEQUENCE CHARACTERISTICS:
            (A) LENGTH: 16 base pairs
            (B) TYPE: Nucleic acid
            (C) STRANDEDNESS:Double
            (D) TOPOLOGY: Unknown (ii) SEQUENCE DESCRIPTION: SEQ ID NO:24:

AACAGCTATG ACCATG                                                               16

(2) INFORMATION FOR SEQ ID NO:25:

(i) SEQUENCE CHARACTERISTICS:
            (A) LENGTH: 20 base pairs
            (B) TYPE: Nucleic acid
            (C) STRANDEDNESS:Double
            (D) TOPOLOGY: Unknown (ii) SEQUENCE DESCRIPTION: SEQ ID NO:25:

CTGAGAGGGG CCCCAGTAAC                                                           20

(2) INFORMATION FOR SEQ ID NO:26:

(i) SEQUENCE CHARACTERISTICS:
            (A) LENGTH: 37 base pairs
            (B) TYPE: Nucleic acid
            (C) STRANDEDNESS:Double
            (D) TOPOLOGY: Unknown (ii) SEQUENCE DESCRIPTION: SEQ ID NO:26:

GACTGCGGCC GCTTTTTTTT TTTTGAAATA TTAAAAA                                        37

(2) INFORMATION FOR SEQ ID NO:27:

(i) SEQUENCE CHARACTERISTICS:
            (A) LENGTH: 31 base pairs
            (B) TYPE: Nucleic acid
            (C) STRANDEDNESS:Double
            (D) TOPOLOGY: Unknown (ii) SEQUENCE DESCRIPTION: SEQ ID NO:27:

CCAGAAACAT AATTGAATTC AGCAGCAATT G          31

(2) INFORMATION FOR SEQ ID NO:28:

(i) SEQUENCE CHARACTERISTICS:
      (A) LENGTH: 18 base pairs
      (B) TYPE: Nucleic acid
      (C) STRANDEDNESS:Double
      (D) TOPOLOGY: Unknown (ii) SEQUENCE DESCRIPTION: SEQ ID NO:28:

CTTTATCCGC CTCCATCC          18

(2) INFORMATION FOR SEQ ID NO:29:

(i) SEQUENCE CHARACTERISTICS:
      (A) LENGTH: 32 base pairs
      (B) TYPE: Nucleic acid
      (C) STRANDEDNESS:Double
      (D) TOPOLOGY: Unknown (ii) SEQUENCE DESCRIPTION: SEQ ID NO:29:

CCAATCGCTG CTGAATTCTA ATTATGTTTC TG          32